(12) United States Patent
Sladek

(10) Patent No.: US 6,679,252 B2
(45) Date of Patent: Jan. 20, 2004

(54) COLLAPSIBLE, DISPOSABLE MDI SPACER AND METHOD

(75) Inventor: David T. Sladek, Tucson, AZ (US)

(73) Assignee: Thayer Medical Corporation, Tucson, AZ (US)

(*) Notice: Subject to any disclaimer, the term of this patent is extended or adjusted under 35 U.S.C. 154(b) by 133 days.

(21) Appl. No.: 09/996,217

(22) Filed: Nov. 28, 2001

(65) Prior Publication Data

US 2002/0129814 A1 Sep. 19, 2002

Related U.S. Application Data

(63) Continuation-in-part of application No. 09/812,222, filed on Mar. 19, 2001, which is a continuation-in-part of application No. 09/357,625, filed on Jul. 20, 1999, now Pat. No. 6,202,643, which is a continuation-in-part of application No. 09/028,260, filed on Feb. 23, 1998, now Pat. No. 6,039,042.

(60) Provisional application No. 60/099,407, filed on Sep. 8, 1998.

(51) Int. Cl.[7] .............................................. A61M 11/00
(52) U.S. Cl. ........................... 128/200.23; 128/200.22
(58) Field of Search ..................... 128/200.23, 200.22, 128/203.12, 203.19, 203.23, 205.24

(56) References Cited

U.S. PATENT DOCUMENTS

| | | | |
|---|---|---|---|
| 3,774,602 A | 11/1973 | Edwards | 128/194 |
| 4,174,712 A | 11/1979 | Moren et al. | 128/173 |
| 4,470,412 A | 9/1984 | Nowacki et al. | 128/200.18 |
| 4,534,343 A | 8/1985 | Nowacki et al. | 128/200.23 |
| 4,637,528 A | 1/1987 | Wachinski et al. | 222/182 |
| 4,641,644 A | 2/1987 | Anderson et al. | 128/200.23 |
| 4,706,663 A | 11/1987 | Makiej | 128/200.18 |
| 4,953,545 A | 9/1990 | McCarty | 128/200.23 |
| 5,012,803 A | 5/1991 | Foley et al. | 128/200.23 |
| 5,385,140 A | 1/1995 | Smith | 128/200.23 |
| 5,571,246 A | 11/1996 | Alldredge | 128/200.23 |
| 5,809,996 A * | 9/1998 | Alldredge | 128/200.23 |
| 5,816,240 A | 10/1998 | Komesaroff | 128/200.23 |
| 6,550,473 B1 * | 4/2003 | Sladek | 128/200.23 |

* cited by examiner

*Primary Examiner*—Weilun Lo
*Assistant Examiner*—Mital Patel
(74) *Attorney, Agent, or Firm*—Cahill, von Hellens & Glazer P.L.C.

(57) ABSTRACT

A disposable, expandable/collapsible medication inhalation apparatus for use with an MDI inhaler includes an elongated housing for receiving a plume of medication particles ejected by the MDI inhaler, a mouthpiece, and an inhalation valve disposed between the mouthpiece and the housing. A pair of foldable side sections are pressed together to expand the apparatus. An exhalation port in the mouthpiece allows exhalation through the mouthpiece. A collapsible boot adapter receives a mouthpiece of the MDI inhaler. The inhalation apparatus is constructed from a single sheet of foldable sheet material.

20 Claims, 21 Drawing Sheets

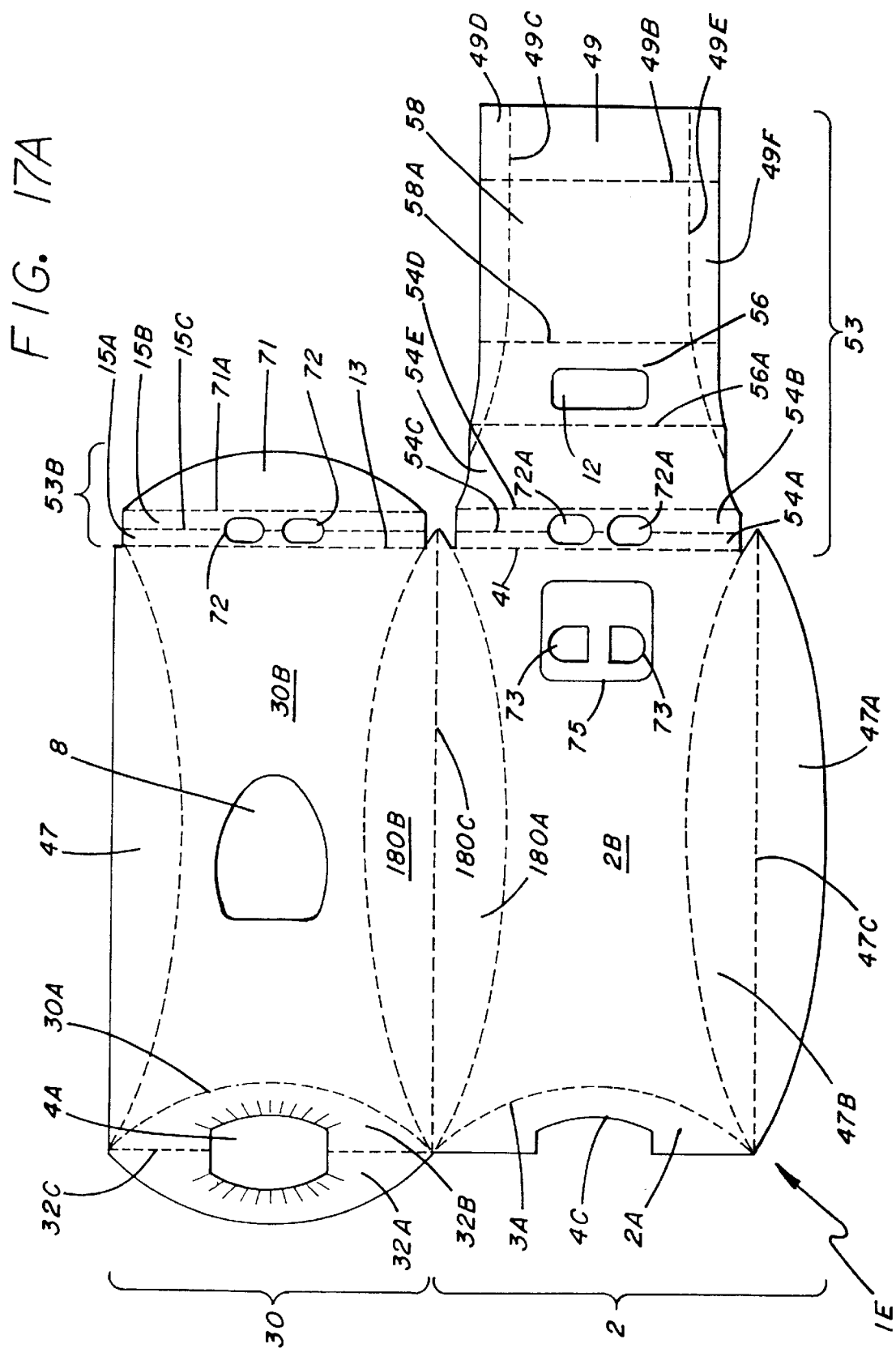

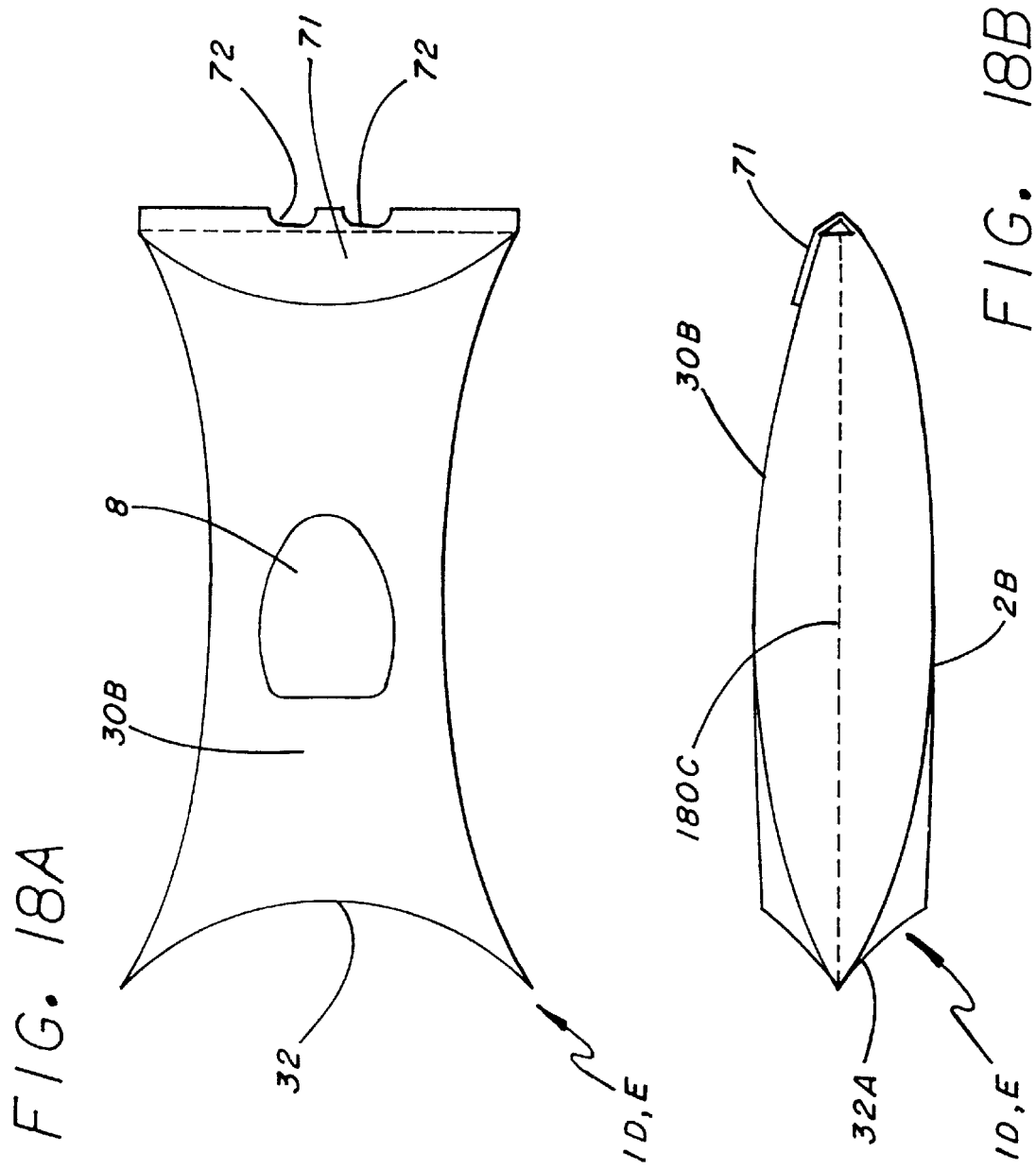

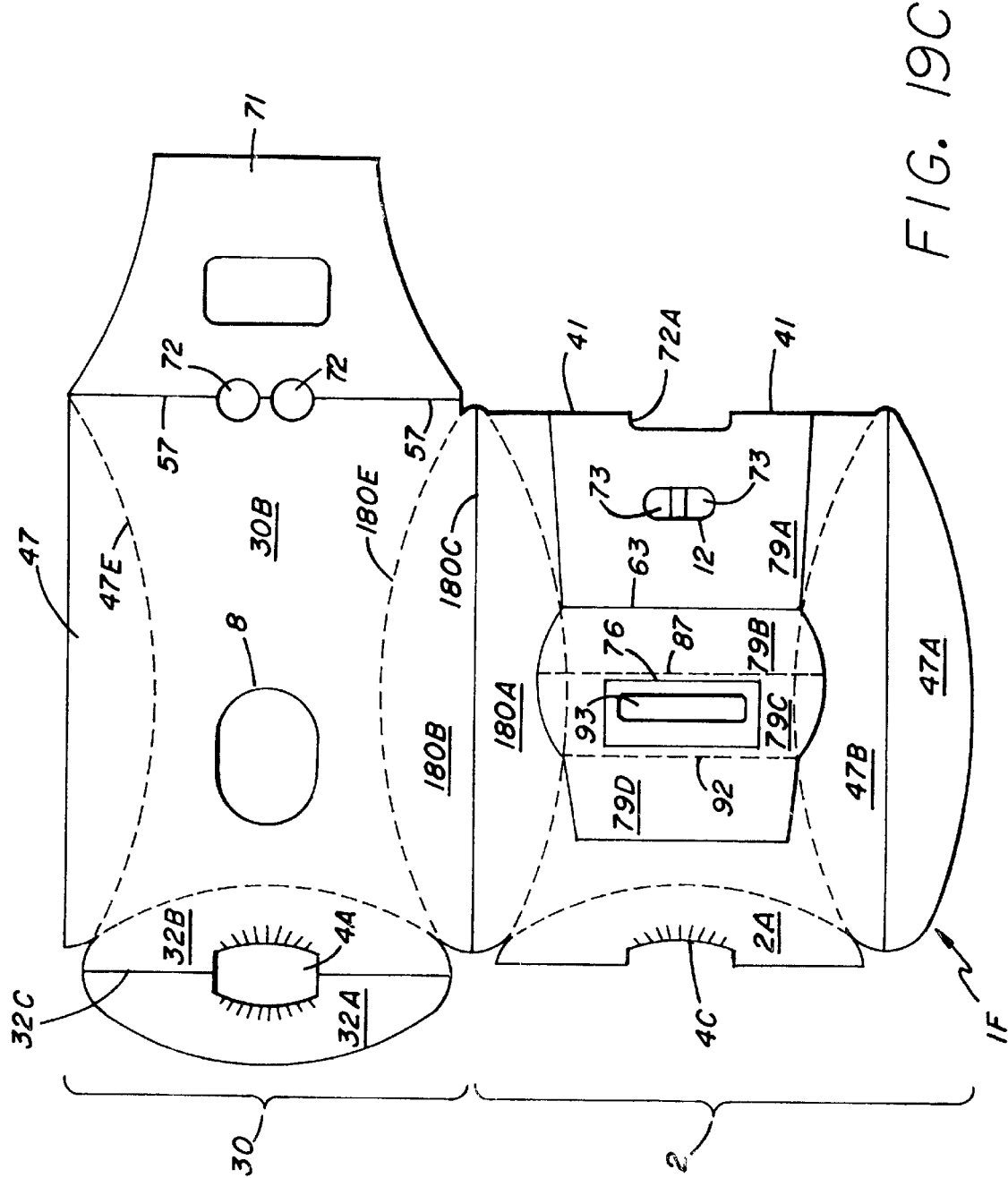

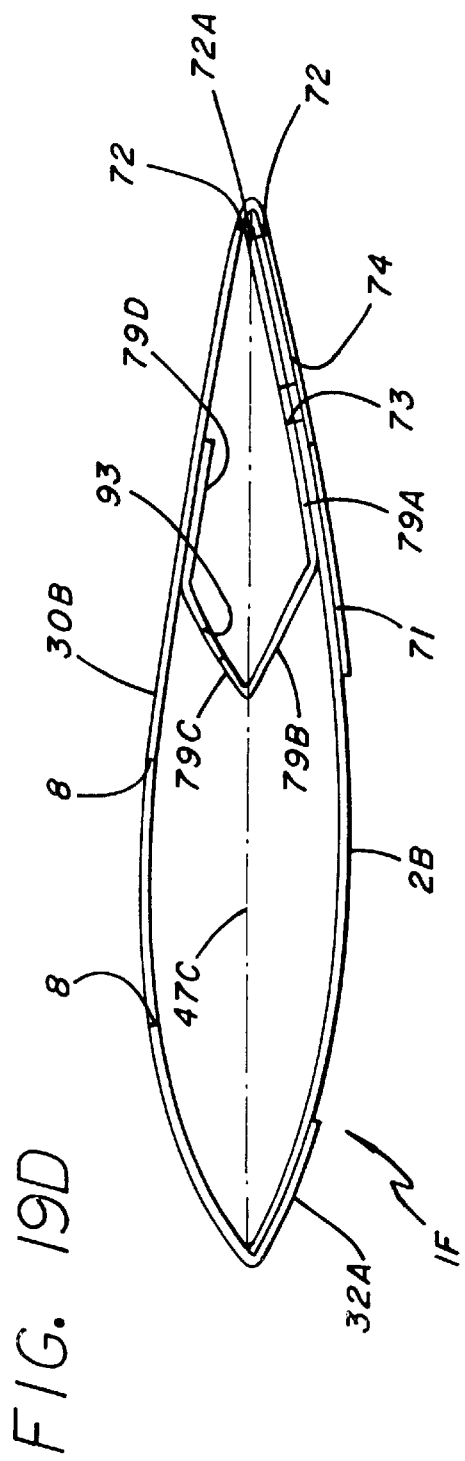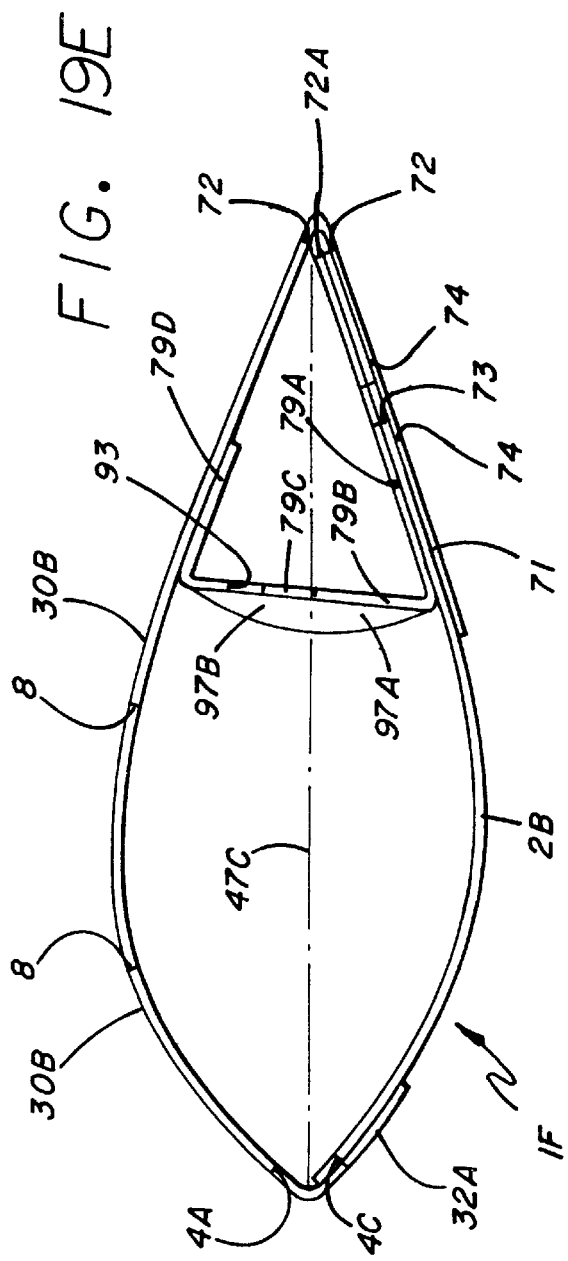

COLLAPSIBLE, DISPOSABLE MDI SPACER AND METHOD

CROSS REFERENCE TO RELATED APPLICATIONS

This application is a continuation-in-part of my commonly assigned patent application entitled "COLLAPSIBLE, DISPOSABLE MDI SPACER AND METHOD", filed Mar. 19, 2001, Ser. No. 09/812,222, which is a continuation-in-part of the patent application entitled "COLLAPSIBLE, DISPOSABLE MDI SPACER AND METHOD", filed Jul. 20, 1999, Ser. No. 09/357,625, now U.S. Pat. No. 6,202,643, issued Mar. 20, 2001, fully incorporated herein by reference, which (1) is a continuation-in-part of my commonly assigned patent application entitled "PORTABLE CHAMBER FOR METERED DOSE INHALER DISPENSERS", filed on Feb. 23, 1998, Ser. No. 09/028,260, now U.S. Pat. No. 6,039,042, issued Mar. 21, 2000, also incorporated herein by reference, and (2) claims the benefit of prior filed co-pending U.S. provisional application Ser. No. 60/099,407 filed Sep. 8, 1998 entitled "COLLAPSIBLE, DISPOSABLE MDI SPACER AND METHOD" by David T. Sladek and Jean W. Keppel.

BACKGROUND OF THE INVENTION

The invention relates to a spacer or valved chamber for delivering aerosol medication from an MDI canister in a dispenser ("boot") supplied by the manufacturer to a patient, through a hand-held chamber operated by the patient, and particularly to an inexpensive collapsible, disposable valved chamber.

MDI drug canisters, which have been used since 1956, are sold with a "boot" that includes an actuator, a nozzle, and a mouthpiece. The patient can self-administer the MDI drug using the boot alone; however, the patient must place the mouthpiece of the boot in or near his/her mouth and inhale exactly when the MDI canister is actuated. This is difficult for some patients. Therefore, various suppliers have provided valved chambers that can be used in conjunction with an MDI boot. Such valved chambers may improve drug delivery by reducing the oropharyngeal deposition of the aerosol drug and by making synchronization of the MDI canister actuation with inhalation of the ejected medication less critical.

A commonly used valved chamber of this type is manufactured by Monaghan Medical Corporation, marketed under the trademark "AEROCHAMBER", and refers to U.S. Pat. Nos. 4,470,412 and 5,012,803. Another similar valved chamber of this type is marketed under the trademark "OPTICHAMBER", described in U.S. Pat. No. 5,385,140 (Smith).

The prior AEROCHAMBER device utilizes only an inhalation valve, so the patient must exhale before placing the device in his/her mouth. That presents a significant problem because it is difficult for many patients to initially perform the required sequence of (1) exhaling, (2) then immediately placing the chamber mouthpiece in his/her mouth, (3) then actuating the MDI canister to inject a medication plume into the valved chamber, and (4) then taking a slow deep breath and holding his/her breath for a few seconds. The prior OPTICHAMBER device provides both an inhalation valve and an exhalation valve, so that device need not be removed from the patient's mouth in order to use it.

A problem of the prior art is that the prior valved chamber devices are far too expensive to be considered disposable, and/or they are not at all collapsible or are insufficiently collapsible to be carried conveniently in a briefcase, vest pocket, or the like. U.S. Pat. Nos. 4,637,528 and 4,641,644 disclose aerosol inhalation devices that are partly collapsible, but not to a generally thin, flat configuration. U.S. Pat. No. 4,953,545 discloses a chamber that is disposable but not collapsible.

The retail cost of prior valved chambers described above typically is as much as nearly $40.00. This cost may be acceptable to patients having chronic conditions that require frequent use of MDI inhaler medication for a long period of time, provided the patients are willing to frequently clean such MDI inhalers. However, many patients need MDI inhaler medications for only a short period of time, in which case the high cost of the prior art valved chambers is very unsatisfactory, especially if a substantially lower cost alternative were available.

Thus, there is an unmet need for an improved valved chamber device which avoids the above mentioned problems of the prior art and provides a portable, light, reliable, inexpensive, disposable, collapsible, easy-to-use valved chamber for use with MDI inhalers. There also is an unmet need for an improved valved chamber device which is sufficiently inexpensive that it can be used as a disposable diagnostic dosing aid, temporary medication delivery aid, or teaching aid for instructing patients in the use of valved chamber devices. There is a further need for such a valved chamber which can be "popped up" from the collapse configuration into an expanded configuration 34 use, and which retains the expanded configuration unless it is manually pressed back into the collapse configuration.

SUMMARY OF THE INVENTION

Accordingly, it is an object of the invention to improve the efficiency of a collapsible/expandable valved chamber device for delivering MDI medications for the like.

It is another object of the invention to prevent a patient using a collapsible/expandable valved chamber from inadvertently blowing MDI medication out of the collapsible/expandable valved chamber if the patient inadvertently exhales while actuating an MDI canister that introduces the medication into the collapsible/expandable valved chamber.

It is another object of the invention to provide an inexpensive, disposable, collapsible valved chamber for delivering MDI medications or vaccines.

It is another object of the invention to provide an inexpensive, disposable valved chamber which is collapsible to a flat configuration.

It is another object of the invention to provide an easily manufacturable valved chamber which is collapsible to a flat configuration.

It is another object of the invention to provide a valved chamber which is sufficiently inexpensive that it can be used as a discardable diagnostic dosing aid, temporary medication delivery aid, or training aid by means of which a health care provider can demonstrate proper techniques for using a permanent valved chamber.

It is another object of the invention to provide a valved chamber which can pop up from a collapsed configuration to an expanded configuration ready for use.

It is another object of the invention to provide a valved chamber which can pop up from a collapsed configuration to an expanded configuration ready for use and retain the expanded configuration.

It is another object of the invention to provide a valved chamber which can be "popped up" or erected from a collapsed configuration by a user with a minimal amount of effort.

It is another object of the invention to reduce the amount of effort required of a user to erect a collapsible/expandable valved chamber.

Briefly described, and in accordance with one embodiment thereof, the invention provides an elongated housing for receiving a plume of medication particles ejected by an MDI inhaler, having a medication inlet end and a medication outlet end, a mouthpiece at the medication outlet end, a one-way inhalation valve disposed between the mouthpiece and a first volume bounded by the housing for allowing flow of gas from the first volume to the mouthpiece, an exhalation port or valve disposed in the mouthpiece for allowing flow of gas from within the mouthpiece to ambient atmosphere outside of the apparatus, an adapter connected to the medication inlet end for receiving and stabilizing a mouthpiece of the MDI inhaler, wherein the one-way inhalation valve includes an inhalation membrane adjacent to a valve seat. An exhalation by a patient into the mouthpiece presses the inhalation membrane against the valve seat to prevent flow of exhaled gas from the mouthpiece into the first volume, causing the exhaled gas to flow from the mouthpiece through the exhalation port or valve. An inhalation from the mouthpiece by the patient causes the inhalation membrane to swing away from the valve seat and allow passage of air from the volume into the mouthpiece.

In one described embodiment, an expandable/collapsible medication inhalation apparatus that can be expanded from an initially flat, collapsed configuration includes a housing in the collapsed configuration, wherein an inhalation/exhalation opening (72) is disposed at an outlet end of the housing and a collapsible/expandable one-way inhalation valve assembly (79) in the housing allows one-way flow of gas from within the housing when it is expanded through the inhalation/exhalation opening (72) during inhalation by a patient. A collapsible/expandable boot adapter panel (32AB) is connected to an inlet end of the housing, and an opening (4A) in the boot adapter panel Receives a mouthpiece of an MDI inhaler. The inhalation valve assembly (79) includes an inhalation flap (76) and a valve seat. An exhalation by the patient through the inhalation/exhalation opening (72) when the housing is expanded presses the inhalation flap (76) against the valve seat to prevent flow of exhaled gas through the inhalation valve assembly (79). The exhaled gas Flows through an opening (73) in the housing between the inhalation valve assembly (79) and the inhalation/exhalation opening (72). The housing, the inhalation valve assembly (79), and the boot adapter panel (32AB) are expanded by pressing a pair of foldable side panels on opposite sides of the housing to unfold the side panels, causing a top panel (30B) of the housing to be pushed away from a bottom panel (2B) of the housing and simultaneously forcing a portion of the inhalation valve assembly 72) to unfold to provide a nearly vertical wall that separates a first volume between the inhalation valve assembly (79) and the boot adapter panel (32AB) and a second volume between the inhalation of assembly (79) and the inhalation/exhalation opening (72).

In the foregoing embodiment, first (97A,B) and second (96A,B) foldable sealing panels are attached along corresponding fold lines to the inhalation valve assembly (79). The first and second foldable sealing panels are engaged by the first (180A,B) and second (47A,B) foldable side sections, respectively, during manual expanding of the housing such that the first and second foldable sealing panels fold against and form seals with the first and second foldable side sections, respectively, to prevent exhaled and/or inhaled gas from bypassing the inhalation valve assembly (79).

BRIEF DESCRIPTION OF THE DRAWINGS

FIG. 17A is a top view of a sheet from which a fifth embodiment of the invention is constructed.

FIG. 18A is a top view of a collapsible/expandable valved chamber constructed of either the sheet shown in FIGS. 16A–C or the sheet shown in FIGS. 17A–C, in its "popped up" configuration.

FIG. 18B is a left side view of a collapsible/expandable valved chamber constructed of either the sheet shown in FIGS. 16A–C or the sheet shown in FIGS. 17A–C, in its "popped up" configuration.

FIG. 19C is a bottom view, drawn to scale, of the sheet as shown in FIG. 19B in which a portion has been folded back to construct an internal inhalation valve structure.

FIG. 19D is a section view of a collapsible/expandable valved chamber constructed of the sheet shown in FIGS. 19A–C in a partially "popped up" configuration.

FIG. 19E is a section view of the collapsible/expandable valved chamber shown in FIG. 19D its fully "popped up" configuration.

DETAILED DESCRIPTION OF THE PREFERRED EMBODIMENTS

Figure 1:
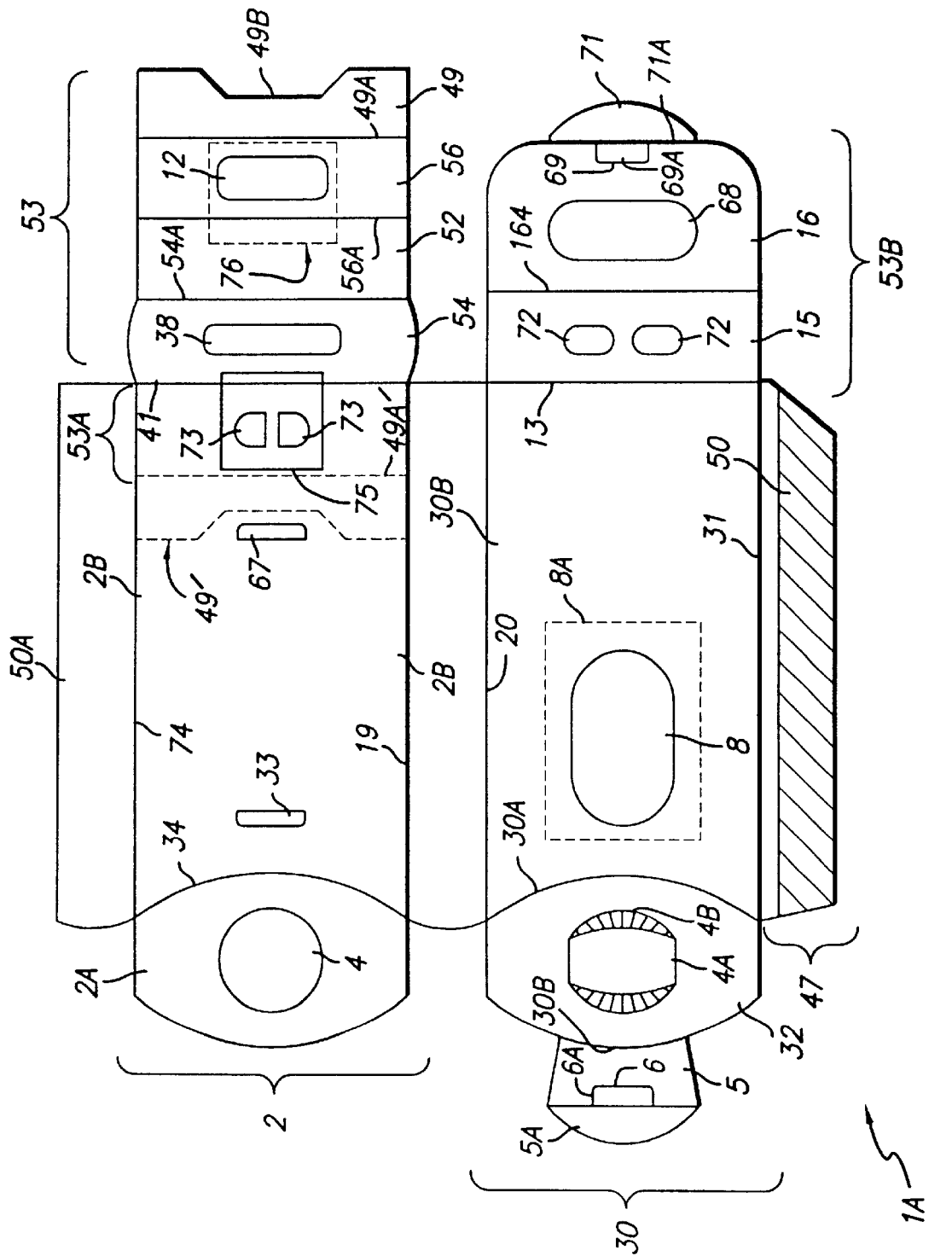
FIG. 1 is a plan view of the outer surface of a sheet from which a first embodiment of the collapsible, disposable valved chamber of the present invention is constructed.
Figure 2:
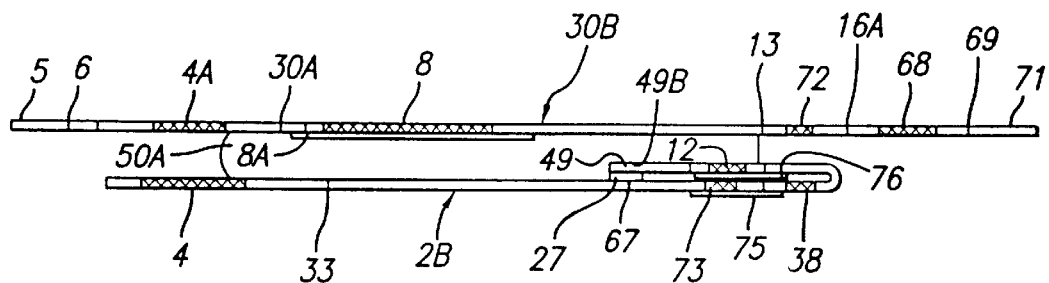
FIG. 2 is a longitudinal section view of the collapsible, disposable valved chamber of FIG. 1 after tabs 50 and 50A have been adhesively attached and the mouthpiece section 53 has been partially folded and adhesively attached and the unit has been folded for shipping.
Figure 3:
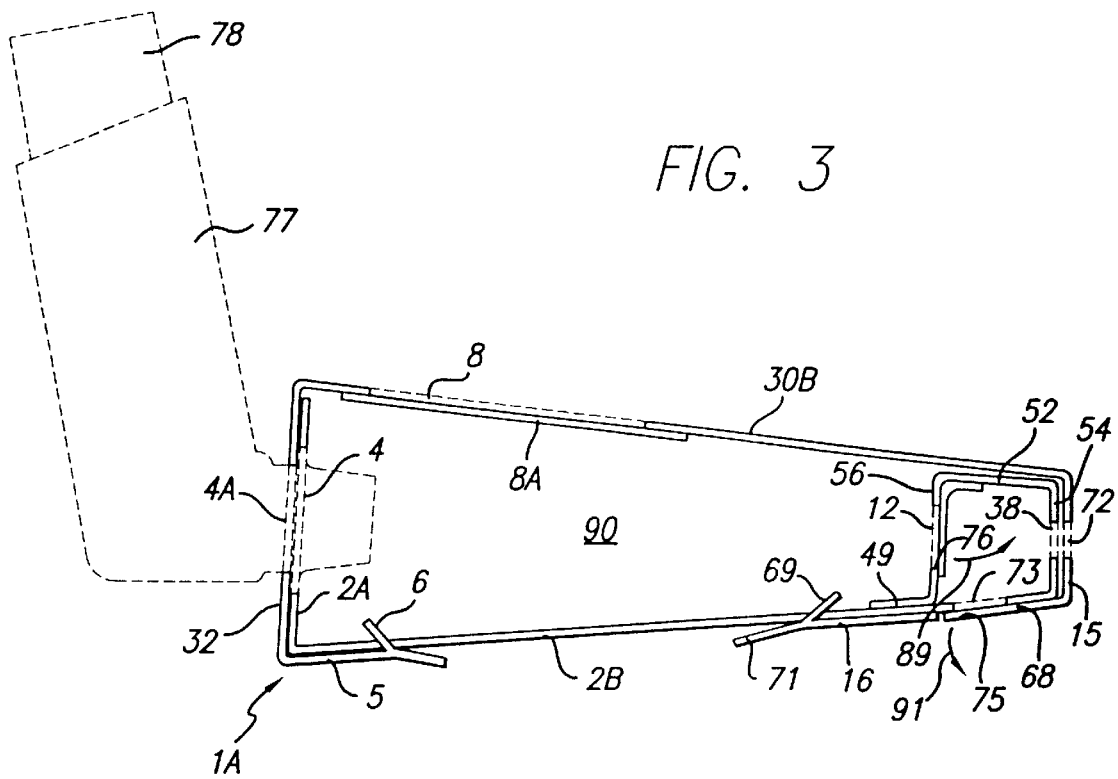
FIG. 3 is a longitudinal section view of the collapsible, disposable valved chamber of FIGS. 1 and 2 erected and ready for use.
Figure 4:
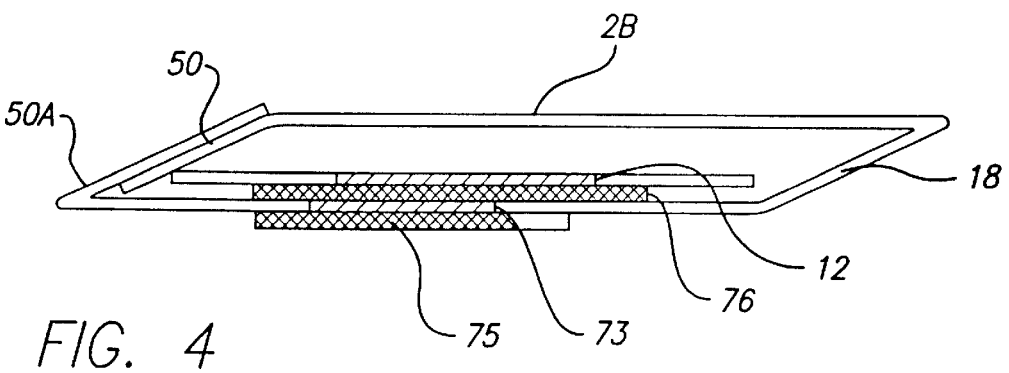
FIG. 4 is a transverse section view of the collapsible, disposable valved chamber compressed for shipping.

FIG. 1 shows the outer surface of a sheet 1A from which a preferred first embodiment of the valved chamber of the present invention is assembled. FIG. 2 shows a longitudinal section view of the assembled chamber, folded or collapsed for shipping. FIG. 4 shows a corresponding transverse section view of the collapsed valved chamber. FIG. 3 shows a longitudinal section view of the chamber assembled, expanded, and ready for use.

Referring to FIGS. 1–4, the entire valved chamber structure, except for the subsequently described inhale valve membrane 76, exhale valve membrane 75, and viewing window membrane 8A, is punched from a single sheet of suitable material, such as paperboard, plastic, spun nonwoven polymer such as TYVEK by DuPont, or the like. Note that reference character 1A is used herein to designate both sheet 1A and the valved chamber assembled therefrom.

It also should be noted that the terms top, bottom, left, right, front, and back or rear are used from the viewpoint of a user of the assembled valved chamber facing the mouthpiece openings 72, with viewing window 8 oriented upward as shown in FIG. 3.

Sheet 1A includes a bottom section 2 connected along a fold line 19 to a right side section 18. Right side section 18 is connected along a fold line 20 to a top section 30. Top section 30 is connected along a fold line 31 to an adhesive tab section 47. An adhesive 50 is provided on section 47.

Bottom section 2 includes an inner boot adapter panel 2A having therein a boot receiving hole 4. Inner boot adapter panel 2A is connected along an arcuate fold line 3A to a bottom panel 2B of bottom section 2. A left side section 50A is attached along a straight fold line 74 to the left edge of bottom section 2.

An exhale valve includes two exhale valve holes 73 in bottom panel 2B and a flexible exhale valve membrane 75, which typically is transparent plastic film, adhesively attached along an edge to the outer surface of bottom panel 2B to cover exhale holes 73.

The front end of bottom panel 2B is connected along straight fold line 41 to an inner mouthpiece section 53. (It should be noted that all of the fold lines illustrated in FIG. 1 are "score lines" punched into the material of which sheet 1A is formed at the same time sheet 1A is punched out of stock material.) Inner mouthpiece section 53 includes a panel 54 with one edge connected along fold line 41 to bottom panel 2B and another opposite edge connected along fold line 54A to a panel 52. Panel 54 has an inner mouthpiece hole 38 punched therein. Inner mouthpiece hole 38 is aligned with two mouthpiece holes 72 in subsequently described panel 15 of outer mouthpiece section 53A when the valved chamber 1A is in its expanded configuration and ready for use. Inner mouthpiece section 53 also includes a panel 56 having an edge connected to panel 52 along fold line 56A. Panel 56 includes an elongated inhale valve hole 12, and is connected along straight fold line 49A to an adhesive attachment panel 49, which has a truncated recess 49B in its outer edge. A flexible inhale valve membrane 76 is adhesively attached along one edge to the inner surface of panel 52 and/or 56. (The term "adhesive" as used herein is intended to include various attachment materials, including true adhesive materials and also materials such as velcro that provide attachment between two surfaces in response to pressing them together.)

Right side panel 18 of sheet 1A is connected between bottom panel 2B and a top panel 30B of top section 30 by two straight horizontal fold lines 19 and 20.

Top section 30 includes an outer boot adapter panel 32 having an arcuate outer edge as illustrated, and is connected to the rear edge of top panel 30B along an arcuate fold line 30A. Outer boot adapter panel 32 includes an elongated opening 4A having semi-circular "scalloped" sections 4B on opposite edges thereof. The scalloped sections 4B are formed by a plurality of spaced slits such as 4C, so that in its assembled, expanded configuration opening 4A of inner boot adapter panel 32 is aligned with circular opening 4 in inner boot adapter panel 2A and the scalloped sections 4B yield to snugly accommodate the outlet end of various conventional MDI canister boots.

The front edge of bottom panel 30B is connected along straight fold line 13 to an outer mouthpiece section 53B. Outer mouthpiece section 53B includes a panel 15 having two openings 72 therein which are aligned with inner mouthpiece opening 38 and with inhale valve opening 12 when the chamber 1A is assembled and expanded. Panel 15 also is connected along fold line 16A to panel 16. Panel 16 has an elongated opening 68 which is aligned with exhale valve openings 73 in bottom panel 2B in the assembled chamber 1A. A pull tab 71 is attached along line 71A to the outer edge of panel 16. A semi-rectangular cut 69 in panel 16 forms a lock tab 69A which is integral with pull tab 71 and fits into lock tab slot 67 in bottom panel 2B.

When sheet 1A is assembled as subsequently explained, inner mouthpiece section 53, the portion of bottom panel 2B indicated by reference numeral 53A, and outer mouthpiece section 53B are included in the "mouthpiece section" of medication inhalation apparatus 1A.

Top panel 30B has an elongated window 8 therein for viewing the interior of valved chamber 1A when it is in its assembled configuration. Dotted line 8A designates a transparent membrane or sheet adhesively attached to the underside of panel 2B as illustrated in FIGS. 1 and 2. Preferably, window material 8A is composed of plastic film.

Outer boot adapter panel 32 of top section 30 includes a lock section 5 connected along arcuate fold line 30B to the outer edge of outer boot panel 32. Lock section 5 includes a pull tab 5A with a semi-rectangular cut 6 that forms a lock tab 6A which fits into lock tab slot 33 in bottom panel 2B. Lock tab slot 33 in bottom panel 2B is positioned relative to scored arcuate fold line 3A to receive locking tab 6A of outer boot adapter panel 32.

Figure 5:
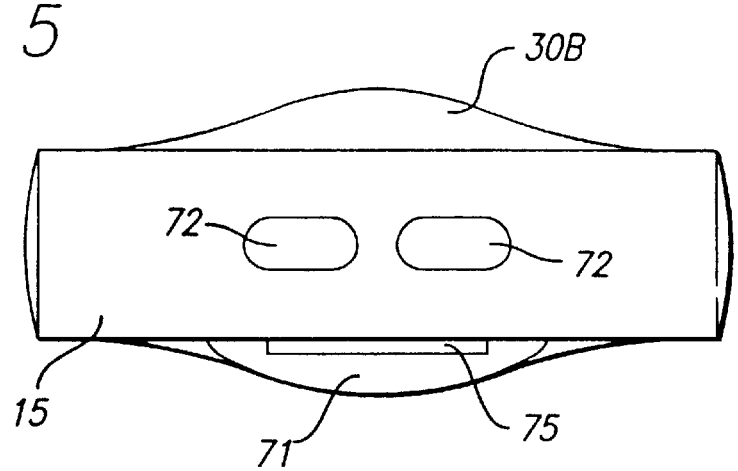
FIG. 5 is an elevational view of the mouthpiece end of the erected structure as shown in FIG. 3.
Figure 6:
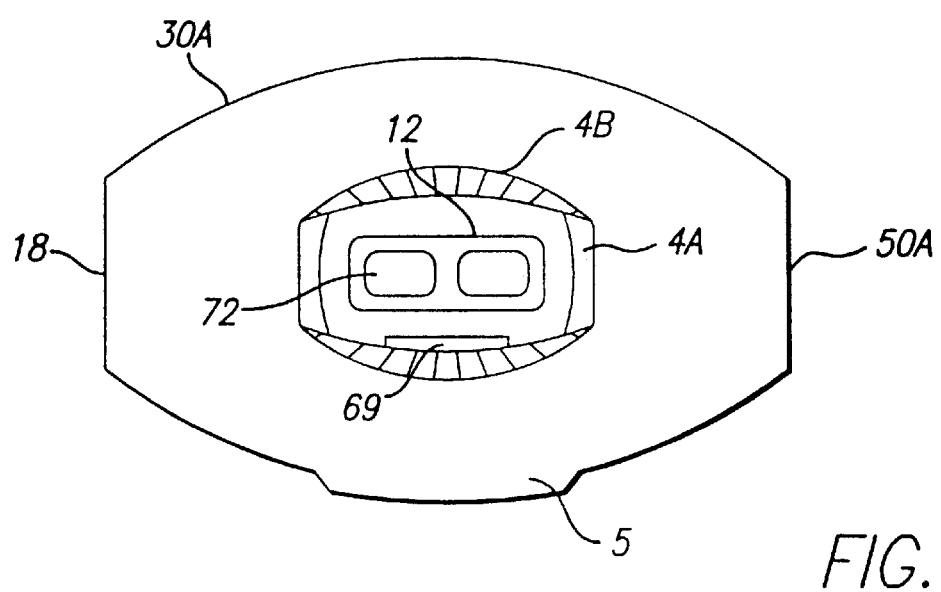
FIG. 6 is an inlet end elevational view of the erected inhaler as shown in FIG. 3.

To assemble sheet 1A into chamber 1A, exhale membrane 75, inhale membrane 76, and window membrane 8A are properly adhesively attached to the inner surface of sheet 1A. Inner mouthpiece section 53 is folded over the inner surface of bottom panel 2B, and the inner surface of panel 49 is adhesively attached by adhesive 27 to the inner surface as shown in FIG. 2. Then, section 47 is attached by adhesive 50 to left edge 50A after bottom section 2 has been folded under top section 30. When top panel 30B is pressed down against bottom panel 2B, a longitudinal section view of the assembled, collapsed chamber 1A appears as shown in FIG. 2. In FIG. 1, dotted lines 49' show the location of panel 49 when its inner surface is adhesively or otherwise attached to the inner surface of bottom panel 2B, and numeral 49A' indicates the corresponding location of fold line 49A. The assembled, collapsed chamber 1A then can be expanded by the user to have the longitudinal cross section shown in FIG. 3 by manipulating the collapsed structure so that sides 18 and 50A are perpendicular to top panel 30B and bottom panel 2B, folding panel 54 up so it and panel 56 are approximately perpendicular to top panel 30B and bottom panel 2B, pulling on pull tab 71 of outer mouthpiece section 53B after drawing panel 16 under bottom panel 2B, to insert lock tab 69 into lock tab slot 67, as shown in FIG. 3. Inner boot adapter panel 2A is bent along arcuate fold line 3A upward so it is approximately perpendicular to top panel 30B and bottom panel 2B. Then outer boot adapter panel 32 is bent down along fold line 30A so it is against inner boot adapter panel 2A and hole 4A is aligned with hole 4. Pull tab 5A is deployed to insert lock tab 6A into lock tab slot 33. The mouthpiece end of assembled and expanded chamber 1A then appears as shown in FIG. 5, and the boot-adapter-receiving end appears as shown in FIG. 6. Chamber 1A is ready to receive the "mouthpiece" end of boot adapter 77.

As shown in FIG. 3, the "mouthpiece" end of the boot adapter 77 of a conventional inhaler containing an MDI canister 78 is inserted through inlet hole 4A of outer boot adapter panel 32 and hole 4 of inner boot adapter panel 2A of assembled and expanded chamber 1A. As the user inhales through aligned mouthpiece openings 38 and 72 of panels 54 and 15, respectively, exhale membrane 75 seals exhale hole 73 and inhale membrane 76 swings to the right in the direction indicated by arrow 89 and a substantial portion of the expanding plume (not shown) of medication particles from MDI canister 78 and a nozzle in boot adapter 77 in the main interior volume 90 of chamber 1A is drawn into the user's mouth. When the user exhales, membrane 76 swings back to its original position to seal inhale opening 12. The exhaled air forces part of exhale membrane 75 to open in the direction of arrow 91, so no exhaled air is forced into volume 90 to be rebreathed.

Figure 7:
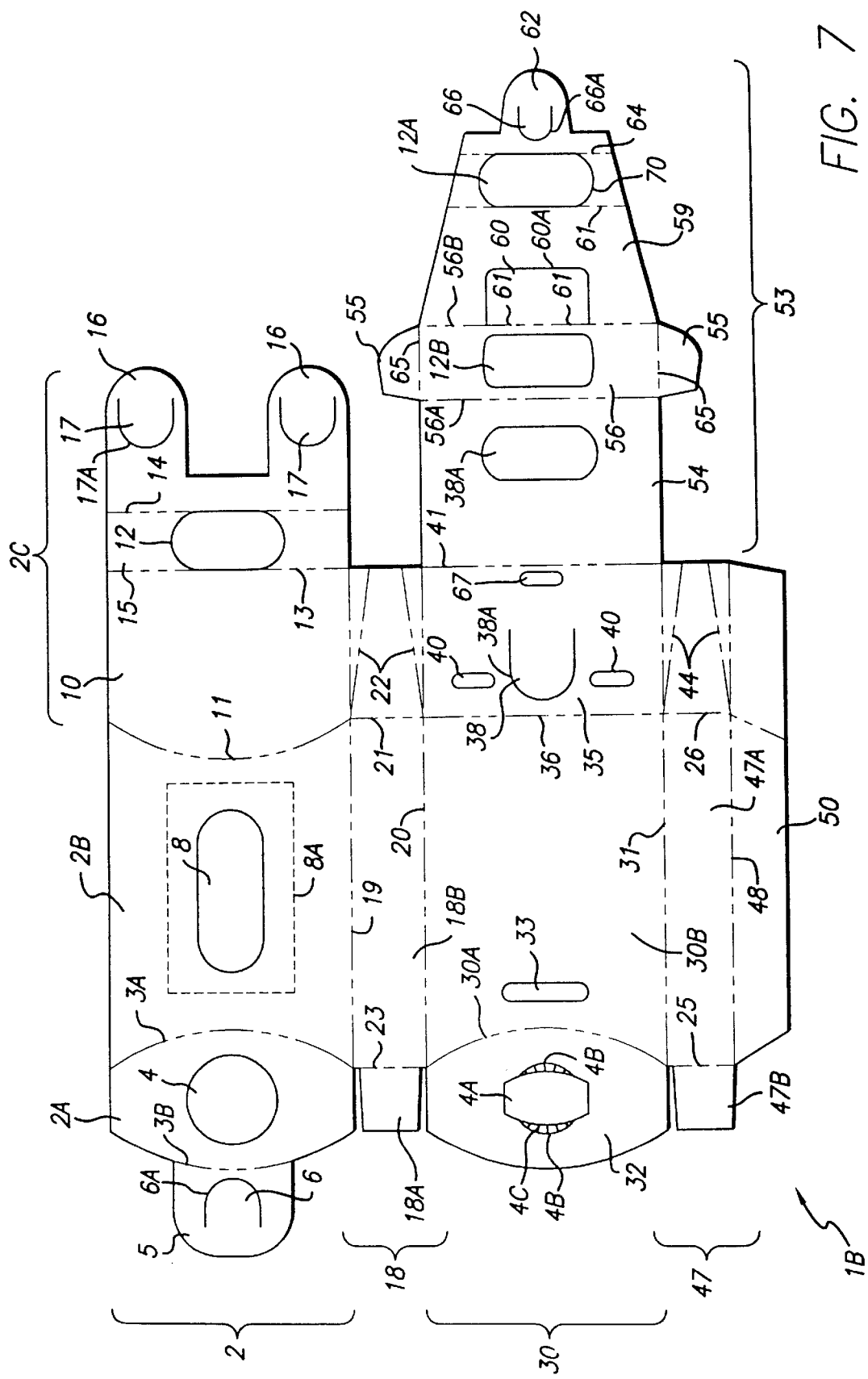
FIG. 7 is a plan view of the outer surface of a sheet from which a second embodiment of the collapsible, disposable valved chamber of the present invention is constructed.

Referring to FIG. 7, a second embodiment of the valved chamber of the invention is disclosed. The same or similar reference characters are used whenever practical to designate similar parts. FIG. 7 shows the outer surface of the sheet 1B from which valved chamber of the present invention is erected or assembled. The entire structure illustrated is punched from a single sheet of suitable material, such as paperboard, plastic, spun nonwoven polymer such as TYVEK or the like. Sheet 1B includes a top section 2 connected along a fold line 19 to a left side section 18. Left side section 18 is connected along a fold this line 20 to a bottom section 30. Bottom section 30 is connected along a fold line 31 to a right side section 47. An adhesive tab 50 is connected along a fold line 48 to right side section 47.

Top section 2 includes an outer boot adapter panel 2A having therein a boot receiving hole 4. Outer boot adapter panel 2A is connected along an arcuate fold line 3A to a top panel 2B and also to a tab 5 along an arcuate fold line 3B. A lock tab 6 formed by an arcuate slit 6A in tab 5 is disposed in tab 5.

Top panel 2B has an elongated window 8 therein for viewing the interior of valved chamber 1B when it is in its "assembled" or expanded or "erected" configuration. (Numeral 1B is used herein to designate both sheet 1B and the valved chamber erected or assembled therefrom.) Dotted line 8A designates a transparent sheet adhesively attached to the underside of panel 2B as illustrated in FIG. 7. Preferably, window material 8A is composed of plastic film. The right end of panel 2B is connected along arcuate fold line 11 to an outer mouthpiece section 2C. All of the fold lines illustrated by dashed lines in FIG. 7 are "score lines" punched into the material of which sheet 1B is formed at the same time sheet 1B is punched out of stock material. Outer mouthpiece section 2C includes a mouthpiece top panel 10. Mouthpiece top panel 10 is connected along a fold line 13 to a mouthpiece end panel 15, which has therein an outer mouthpiece opening 12, as shown. Mouthpiece end panel 15 is connected along a fold line 14 to a locking panel including two spaced apart tabs 16. Each tab 16 includes a lock tab 17 formed by a slit 17A and tab 16.

Left side section 18 includes a tab 18A connected by a vertical fold line 23 to a left side panel 18B. The other end of left side panel 18B includes a vertical fold line 21 and two inclined, perforated fold lines 22 to form a trapezoid, as shown. Their function will be described hereinafter, to establish the taper or slope of upper mouthpiece top panel 10 when the valved chamber 1B is fully expanded.

Bottom section 30 includes an inner boot adapter panel 32 having an arcuate left edge as illustrated, and is connected to bottom panel 30B along an arcuate scored fold line 30A, as shown. Inner boot adapter panel 32 includes an elongated opening 4A having semi-circular "scalloped" portions 4B on opposite edges thereof. The scalloped sections 4B are formed by a plurality of spaced slits such as 4C, so that in its constructed, expanded configuration opening 4A of inner boot adapter panel 32 is aligned with circular opening 4 in outer boot adapter panel 2A and the scalloped portions 4B yield, to snugly accommodate the outlet end of a conventional MDI canister boot.

Bottom section 30 includes bottom panel 30B having an edge connected along fold line 30A to inner boot adapter panel 32, as shown. The other edge of bottom panel 30B is connected along scored fold line 36 to mouthpiece bottom panel 35, which is also connected along scored fold line 41 to the edge of inner mouthpiece section 53, as shown. Mouthpiece bottom panel 35 has two vertical slots 40 adjacent to fold line 36 as shown to receive locking tabs 17 of outer mouthpiece section 2C when valved chamber 1B is constructed in its expanded configuration. An exhale valve tab 38 is formed by a U-shaped slit 38A in mouthpiece bottom panel 35, as shown. An optional vertical slot 67 is for receiving subsequently described optional lock tab 66 in pull tab 62.

Slot 33 in bottom panel 30B is centered relative to scored arcuate fold line 30A and receives locking tab 6 of top section 2.

Inner mouthpiece section 53 includes a fold-back panel 54 which has the same rectangular size and shape as mouthpiece bottom panel 35. An exhale hole 38A is approximately centered in fold-back panel 54 as shown, so that exhale hole 38A is aligned with exhale valve tab 38 when panel 54 is folded back against and adhesively attached to mouthpiece bottom panel 35. When valved chamber 1B is constructed in its expanded configuration, locking tabs 17 slide into slots 40 and thus slip in between panel 54 and panel 35.

Inner mouthpiece section 53 is connected at its midsection along a scored fold line 56A to an inhale valve panel 56 having an inhale valve opening 12B centered therein, as shown. An edge of inhale valve panel 56 is connected along a vertical fold line 56B to a generally trapezoidal panel 59, as shown. An inhale valve flap 60 is hingeably connected to valve panel 56 along fold line 56B by a plurality of short, spaced hinge points 61. The rest of valve flap 60 is surrounded by a slit 60A punched through trapezoidal panel 59 so flap 60 is quite freely hinged to inhale valve panel 56. Alternatively, inhale valve panel 56 can be thin, flexible plastic adhesively, hingeably attached along one side to panel 56 to cover an inhale hole in panel 56 during exhaling and swing away to uncover such inhale hole during inhaling.

Trapezoidal panel 59 contains a mouthpiece end panel 70 having a mouthpiece opening 12A generally centered therein as illustrated. Trapezoidal panel 59 is connected by a scored fold line 64 to a pull tab 62 having an optional U-shaped locking tab 66 formed therein by a U-shaped slit 66A.

Right side section 47 includes a fold tab 47B having one edge connected along a scored fold line 25 to an elongated right side panel 47A. Right side panel 47A is connected at another edge to a portion including a vertical, scored fold line 26 and two inclined perforated fold lines 44 forming a trapezoid, similarly to the above described trapezoid formed by fold lines 21 and 22 in left side section 18.

Figure 8:
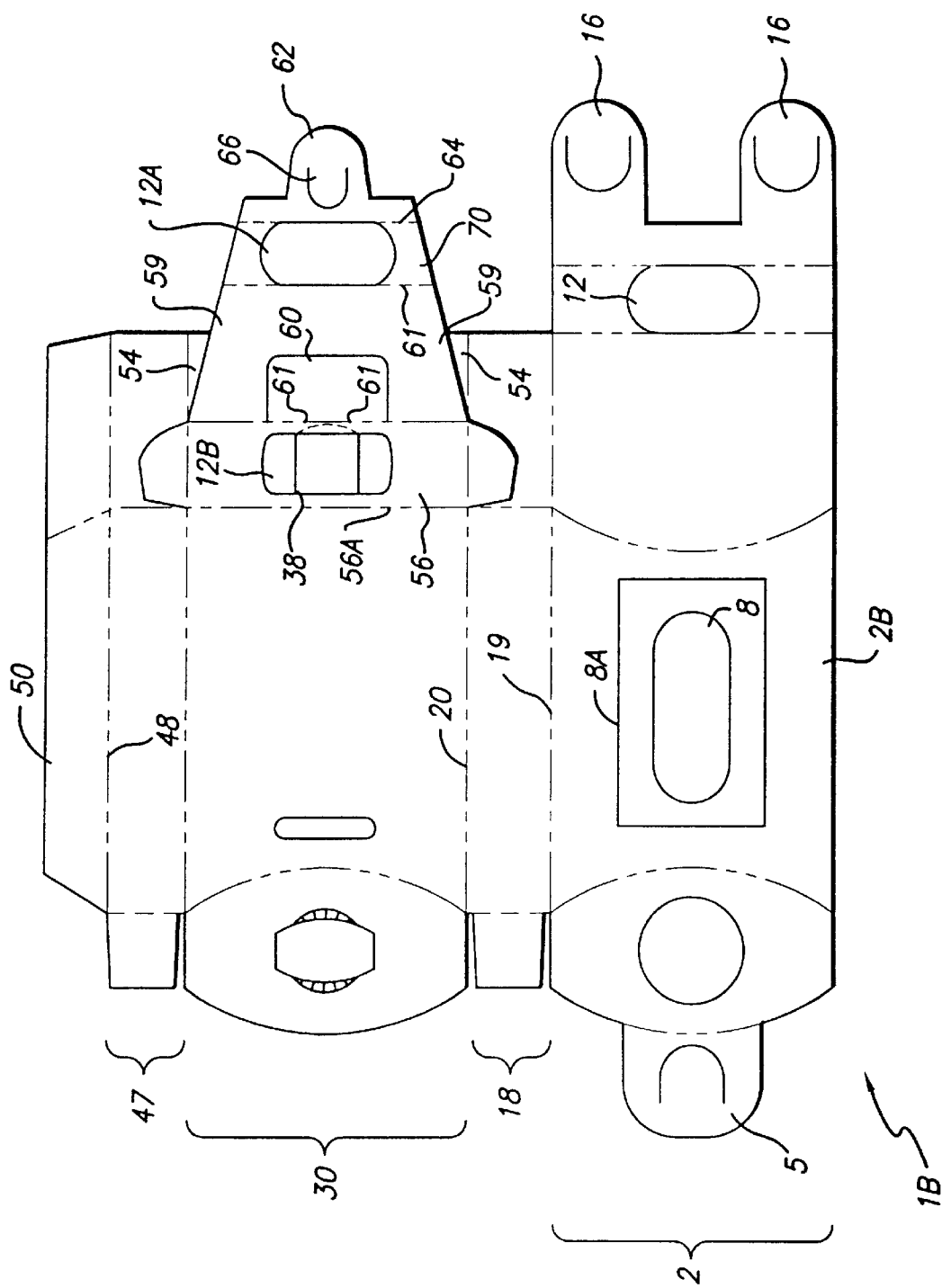
FIG. 8 is a plan view of the inner surface of the sheet of FIG. 1, with the mouthpiece pullout section 53 of FIG. 7 partially folded back and adhesively attached, the rest being positioned in a collapsed configuration.

Referring to FIG. 8, which shows the inner surface of sheet 1B, the first step in the "assembly" or "constraction" of the valved chamber 1B according to the present invention is to fold the inner surface of fold-back panel 54 along scored fold line 41, press it against the inner surface of mouthpiece bottom panel 35, and adhesively attach those two surfaces together. The remaining portions of mouthpiece section 53, including inhale valve panel 56, trapezoidal panel 59, and pull tab 62, are folded back along fold line 56A, as shown in FIG. 2. In this configuration, exhale valve opening 38A is generally aligned with exhale valve flap 38.

The next step is to fold top section 2 and left side section 18 along fold line 20, over and parallel to bottom section 30 and right side section 47, so that the cut edge of top section 2 as shown in FIG. 8 is aligned with scored fold line 48. Then adhesive tab 50 is folded over the outer surface of the cut edge of top section 2 along scored fold line 48 and adhesively attached thereto. This provides the collapsed structure, ready to be shipped.

Figure 9:
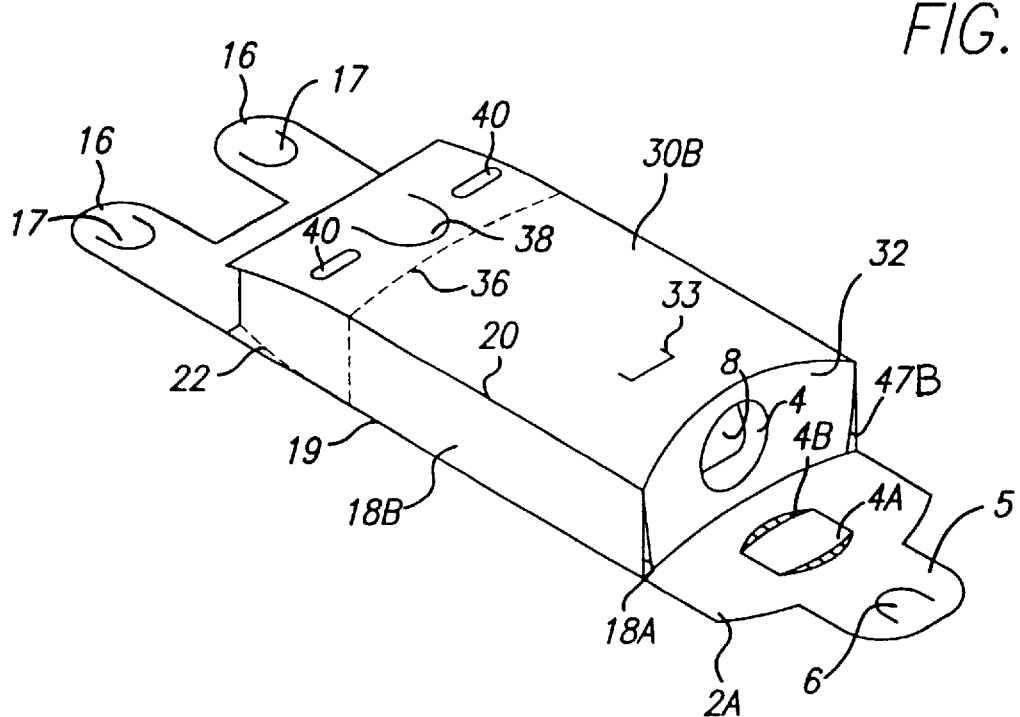
FIG. 9 is a perspective view illustrating "assembly" of the boot adapter end of the valved chamber.

Referring next to FIG. 9, the next step in the construction is to fold tabs 18A and 47B (FIG. 7) inward and then fold inner boot adapter panel 32 upward along scored arcuate fold line 30A as shown. Then, outer boot adapter panel 2A is folded downward along scored arcuate fold line 3A, as shown, and locking tab 6 of tab 5 is inserted into slot 33.

Figure 10:
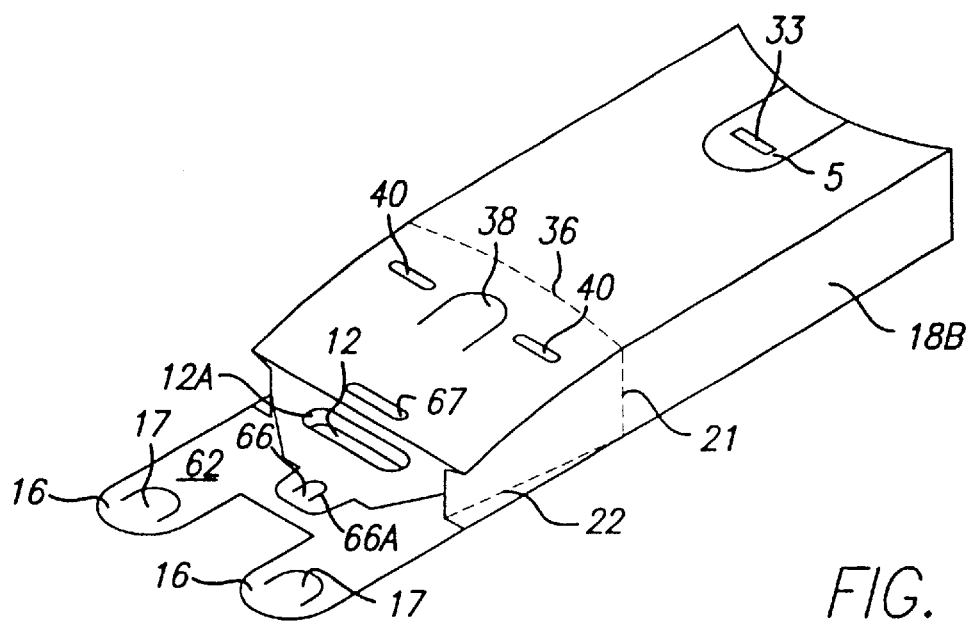
FIG. 10 is a perspective view illustrating "assembly" of the mouthpiece section of the valved chamber.

Referring to FIG. 10, pull tab 62 is pulled outward, causing inhale valve panel 56 to be erected into a vertical position, with tabs 55, which are folded along fold lines 65, acting as stops. Trapezoidal panel 59 and pull tab 62 appear as shown. The next to last step in the expansion of valved chamber 1B is to fold pull tab 62 along fold line 64 as shown and insert optional locking tab 66 of pull tab 62 into slot 67.

The final step in the construction is to pull outer mouthpiece end panel 15 and tabs 16 over and around the end of mouthpiece pull-out section 53, and insert locking tabs 17 into slots 40.

Figure 11:
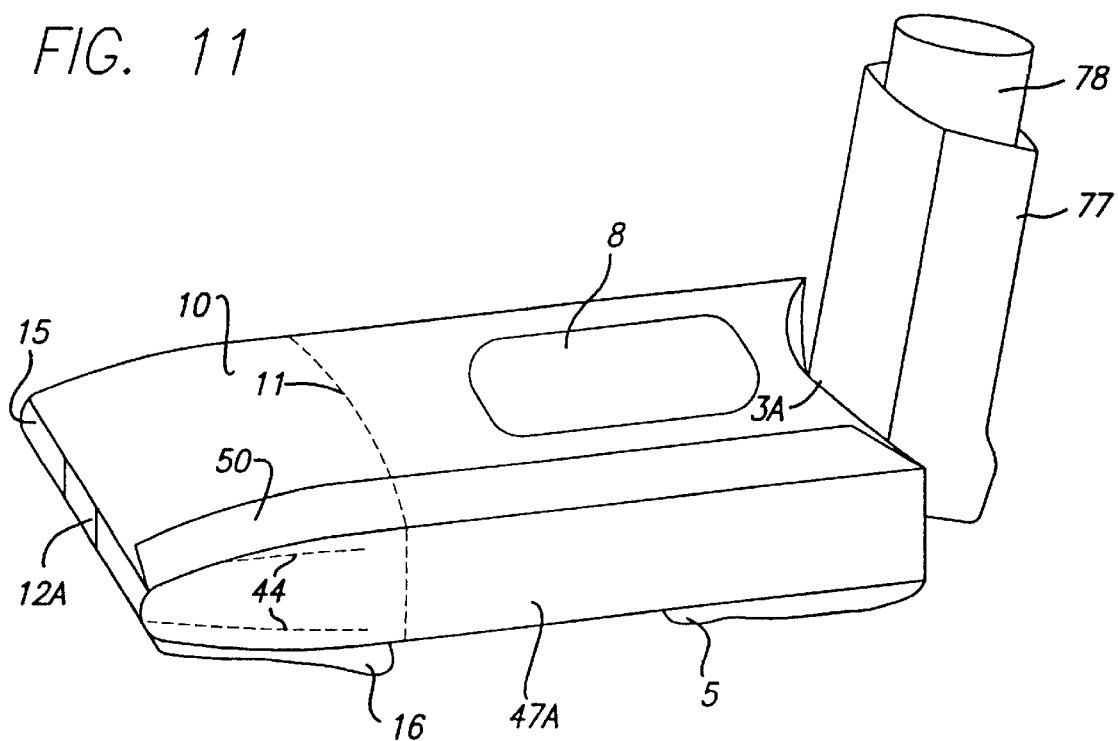
FIG. 11 is a partial perspective view of the valved chamber of FIG. 7 in its expanded configuration, with the boot of an MDI inhaler inserted.

Next, the mouthpiece end of an MDI boot 77 as shown in FIG. 11 is inserted into the aligned openings 4 and 4A of boot adapter panels 2A and 32, respectively. The valved chamber 1B then is ready for use by the patient by simultaneously inhaling while actuating the MDI canister 78 in MDI boot 77. MDI canister 78 ejects a medication plume into the interior volume of valved chamber 1B, which is visible to the patient through window 8. The relative vacuum created by the patient's inhaling causes inhale flap 60 to pivot or swing away from opening 12B in inhale valve panel 56, so a substantial portion of the ejected plume passes through inhale valve opening 12B and mouthpiece end opening 12A into the mouth of the patient.

When the patient exhales before repeating the above procedure, inhale flap 60 is forced, by the increased pressure caused by the exhaling, against the peripheral portion of inhale panel 56 around opening 12B, so that the exhaled air flows through the opening 38A in fold-back panel 54. As the exhaled air flows through exhale opening 38A, it pushes exhale flap 38 outward so that the exhaled air escapes to the outside atmosphere. Similarly to inhale flap 60 described above, exhale flap 38 could alternatively be formed of thin, flexible plastic adhesively, hingeably attached to cover and seal an exhale hole during inhaling by the patient and pivot away from the exhale hole during exhaling by the patient.

Figure 12:
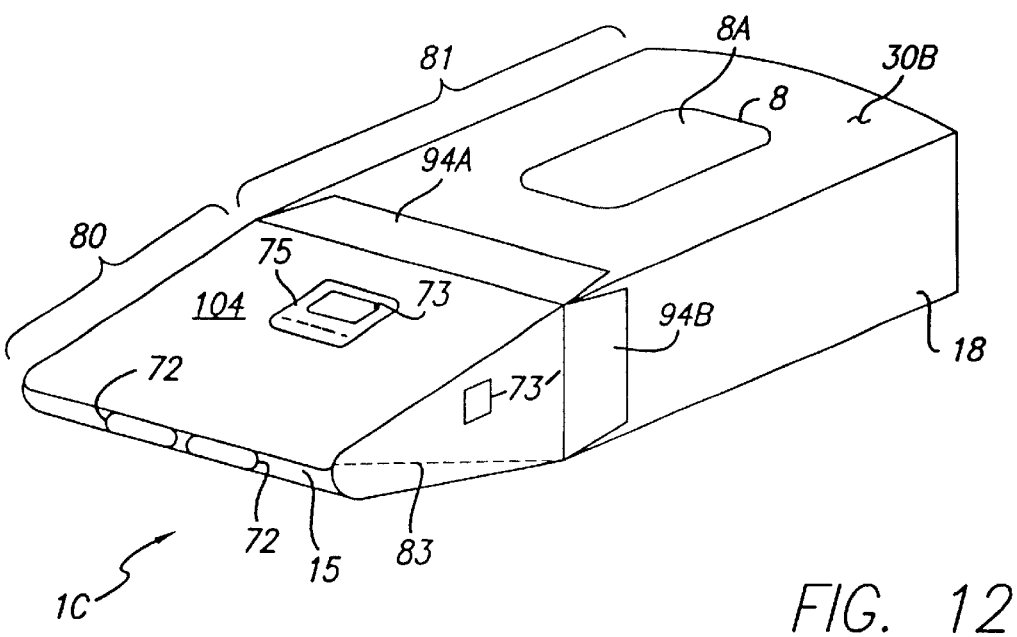
FIG. 12 is an upper front left perspective view of a third embodiment of a collapsible, disposable valved chamber of the present invention, shown in assembled form.

Referring to FIGS. 12–15, a third embodiment of the collapsible, disposable valved chamber is designated by numeral 1C. Where appropriate, the same or similar reference numerals are used as in the embodiment of FIGS. 1–6 to designate the same or corresponding parts. In FIG. 12, chamber 1C includes two main parts 80 and 81, which are separately punched out of a sheet of suitable paper or plastic material, and then are adhesively attached together to provide a disposable collapsible spacer which may be packaged and shipped in a flat configuration and then assembled into an expanded configuration for use by the patient. Numeral 80 in FIGS. 12–15 designates one of the two sections referred to as the "mouthpiece section". Numeral 81 designates a second section referred to as the "chamber section", which includes a collapsible end section 100 that automatically folds when chamber section 81 and mouthpiece section 80 are collapsed as a unit. Mouthpiece section 80 has four attachment flaps 94A–94D which are adhesively attached to the outer edge portions of panels 30B, 18, 2B, and 50A, respectively, of chamber section 81.

Figure 13:
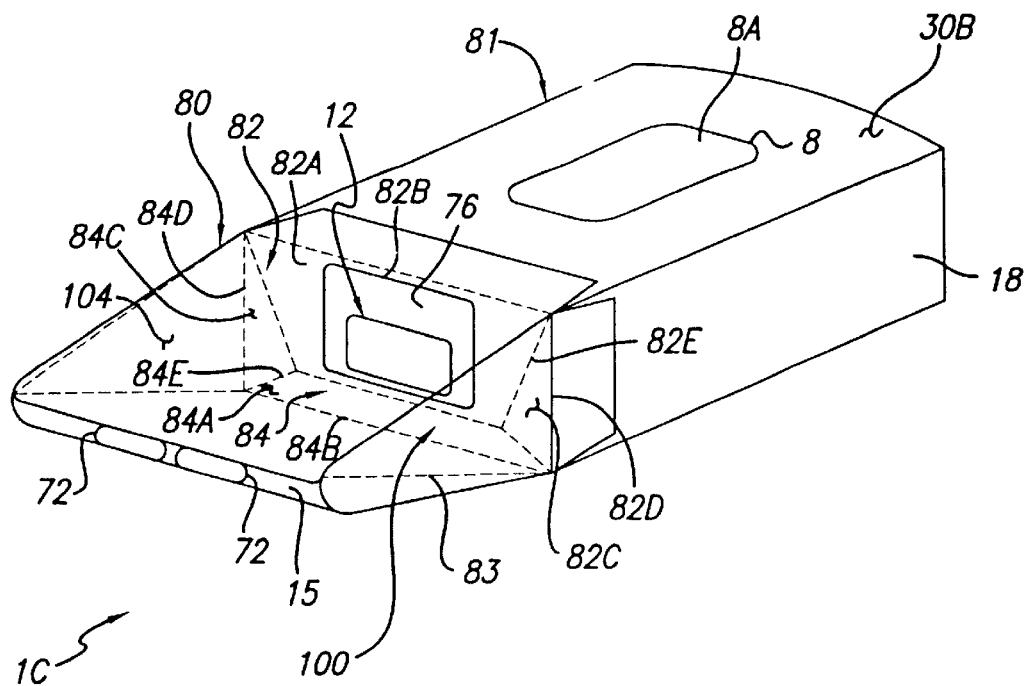
FIG. 13 is a perspective partial see-through view of the embodiment of FIG. 12 with dotted lines illustrating the inhalation port structure.
Figure 14:
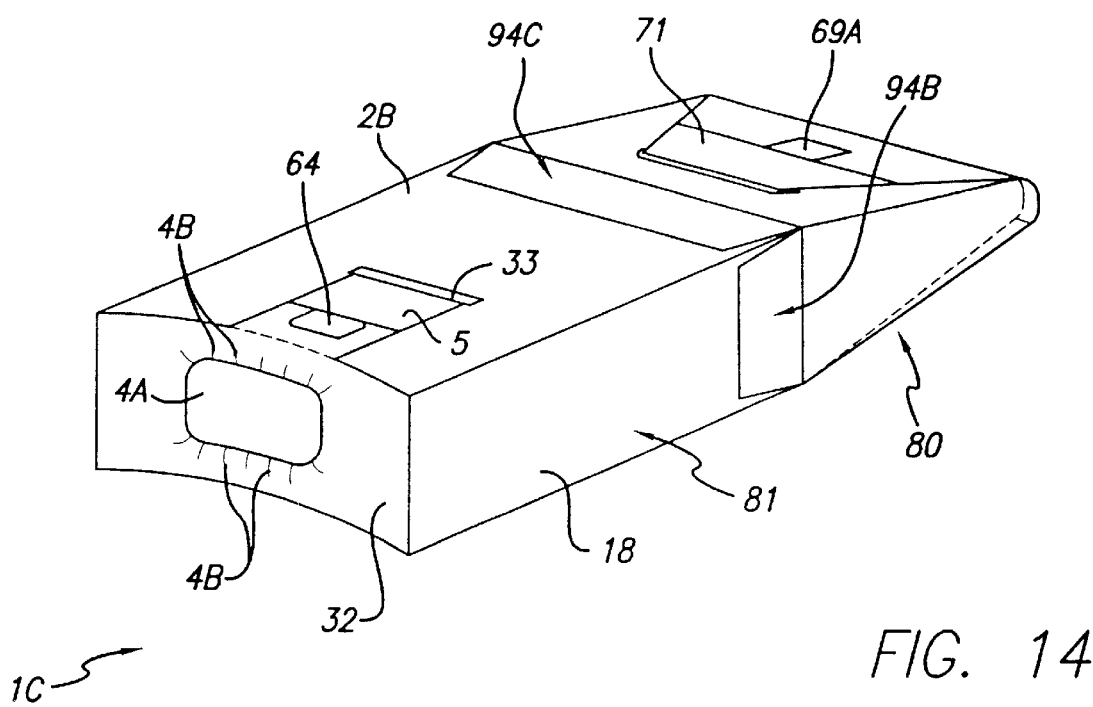
FIG. 14 is a perspective view of the bottom, side, and inlet ends of the valved chamber of FIGS. 12 and 13.

Referring to the partial "see through" view of FIG. 13, collapsible end section 100 is referred to as "autobottom" 100, and includes an upper flap 82 having a first section 82A connected along a straight horizontal first fold line 82B to top panel 30B of chamber section 81 and a second section 82C connected along a straight vertical fold line 82D to right side panel 18. To allow collapsing of autobottom 100, second section 82C of upper flap 82 is connected to first section 82A along an oblique fold line 82E. First section 82A of upper flap 8 has an inhalation hole 12 therein, with the upper edge of an inhale membrane 76 adhesively attached to the front face of first section 82A of upper flap 82, as shown in FIG. 13. The lower portion of inhale membrane 76 covers and seals inhalation hole 12 during exhalation by the patient and swings toward mouthpiece inhalation hole 72 when the user inhales. When chamber section 81 is collapsed, first section 82A and second section 82C of upper flap 82 fold inwardly into chamber section 81 along fold lines 82B, 82D, and 82E.

Figure 15:
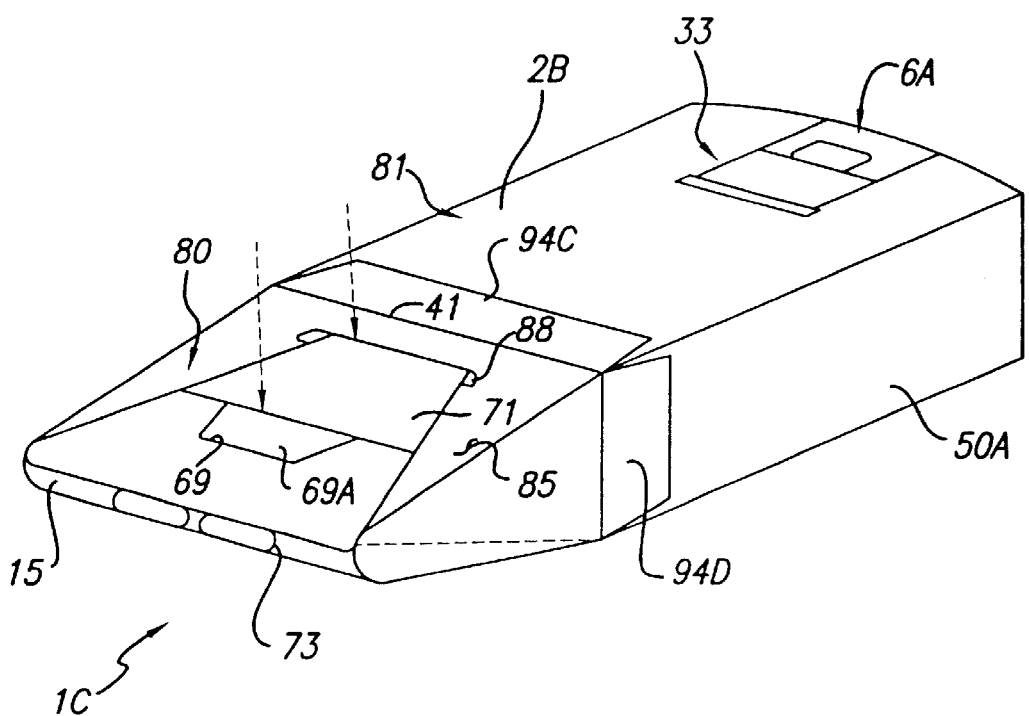
FIG. 15 is a perspective view showing the bottom, side, and mouthpiece ends of the valved chamber of FIGS. 12–14.

Autobottom section 100 also includes a similar lower flap 84 having a first section 84A connected along a straight horizontal first fold line 84B to bottom panel 2B of chamber section 81 and a second section 84C connected along a straight vertical fold line 84D to right side panel 50A indicated in FIG. 15. Referring to FIG. 13, to allow collapsing of autobottom 100, second section 84C is connected to first section 84A along an oblique fold line 84E. When chamber section 81 and mouthpiece section 80 are assembled, lower flap 84 is in front of upper flap 82. The inner surface of lower panel 84 abuts the outer surface of upper flap 82 so as to form a seal with the portion of upper flap 82 below inhale valve membrane 76, leaving inhale valve membrane 76 free to swing toward inhalation openings 72 when the user inhales. When chamber section 81 is collapsed, first section 84A and second section 84C of lower flap 84 fold inwardly behind inwardly folding upper flap 82 into chamber section 81 along fold lines 84B, 84D, and 84E.

Referring to FIGS. 12–15, mouthpiece section 80 includes an inclined top panel 104 and an end panel 15 in which above mentioned inhalation holes 72 are formed as shown in FIG. 12. Mouthpiece section 80 also includes an inclined bottom panel 85 as shown in FIG. 15. Inclined fold lines such as 83 allow the side panels of mouthpiece section 80 to fold slightly inward so that top panel 104 and bottom panel 85 taper to the height of mouthpiece end panel 15 as shown. An exhalation valve hole 73 is provided in top panel 104, and the lower edge of an exhale membrane 75 is adhesively attached to the outer surface of top panel 104 to seal exhalation valve opening 73 when the user inhales, and to swing away from exhalation valve opening 73 when the user exhales. Numeral 73' in FIG. 12 indicates an alternative location for exhalation valve hole 73.

Figure 16A:
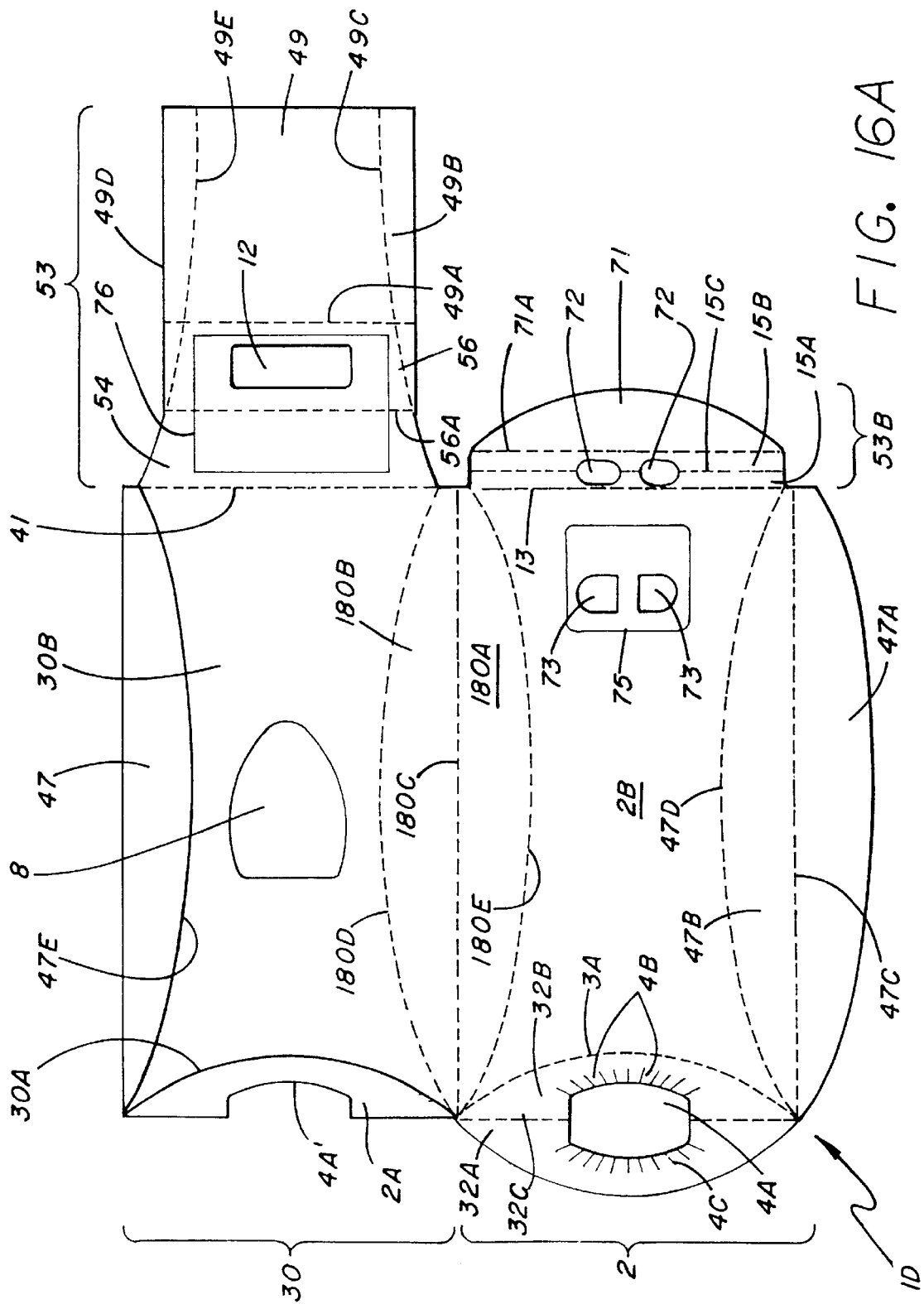
FIG. 16A is a top view of a sheet from which a fourth embodiment of the invention is constructed.
Figure 16B:
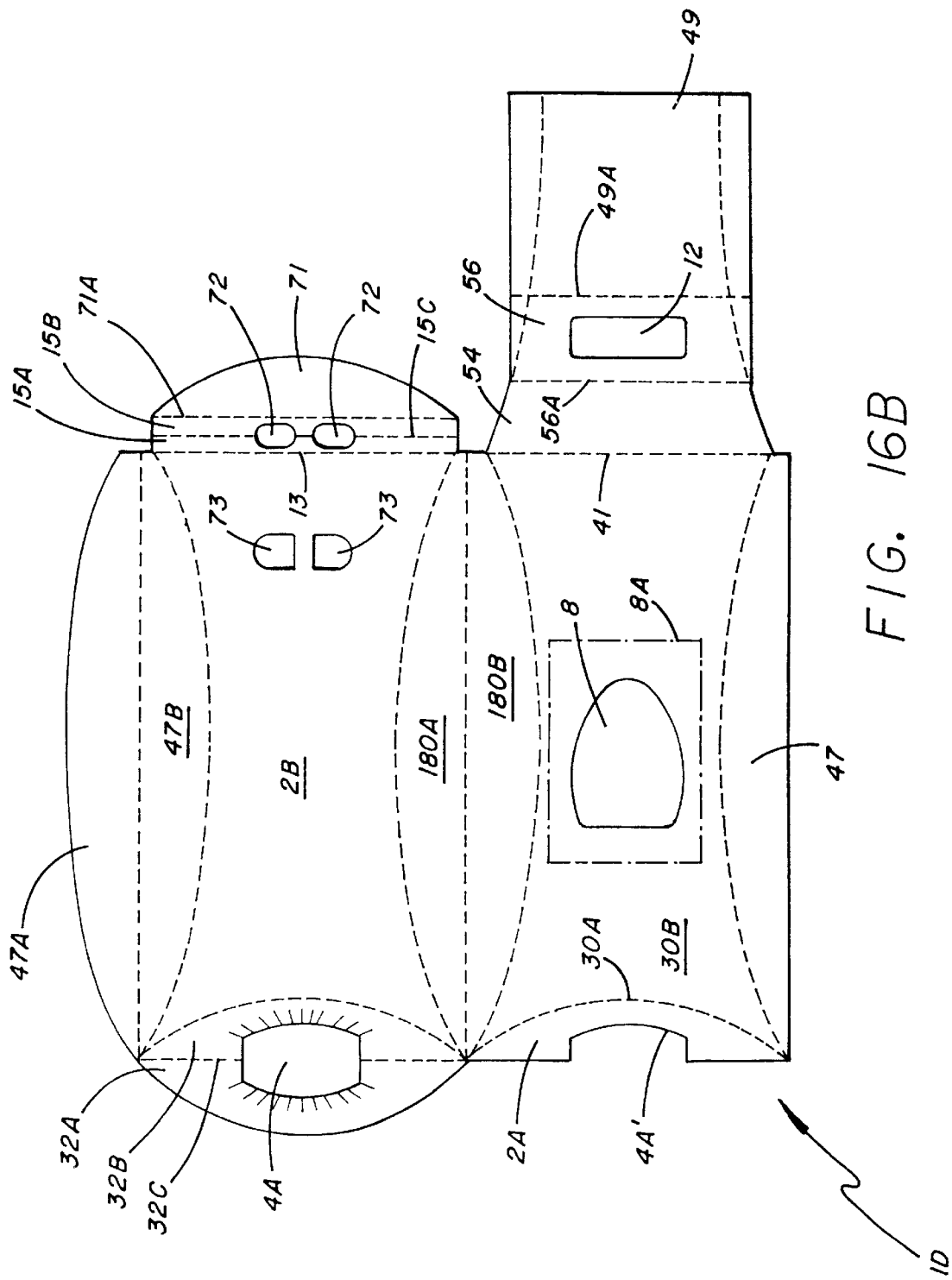
FIG. 16B is a bottom view of the sheet shown in FIG. 16A.
Figure 16C:
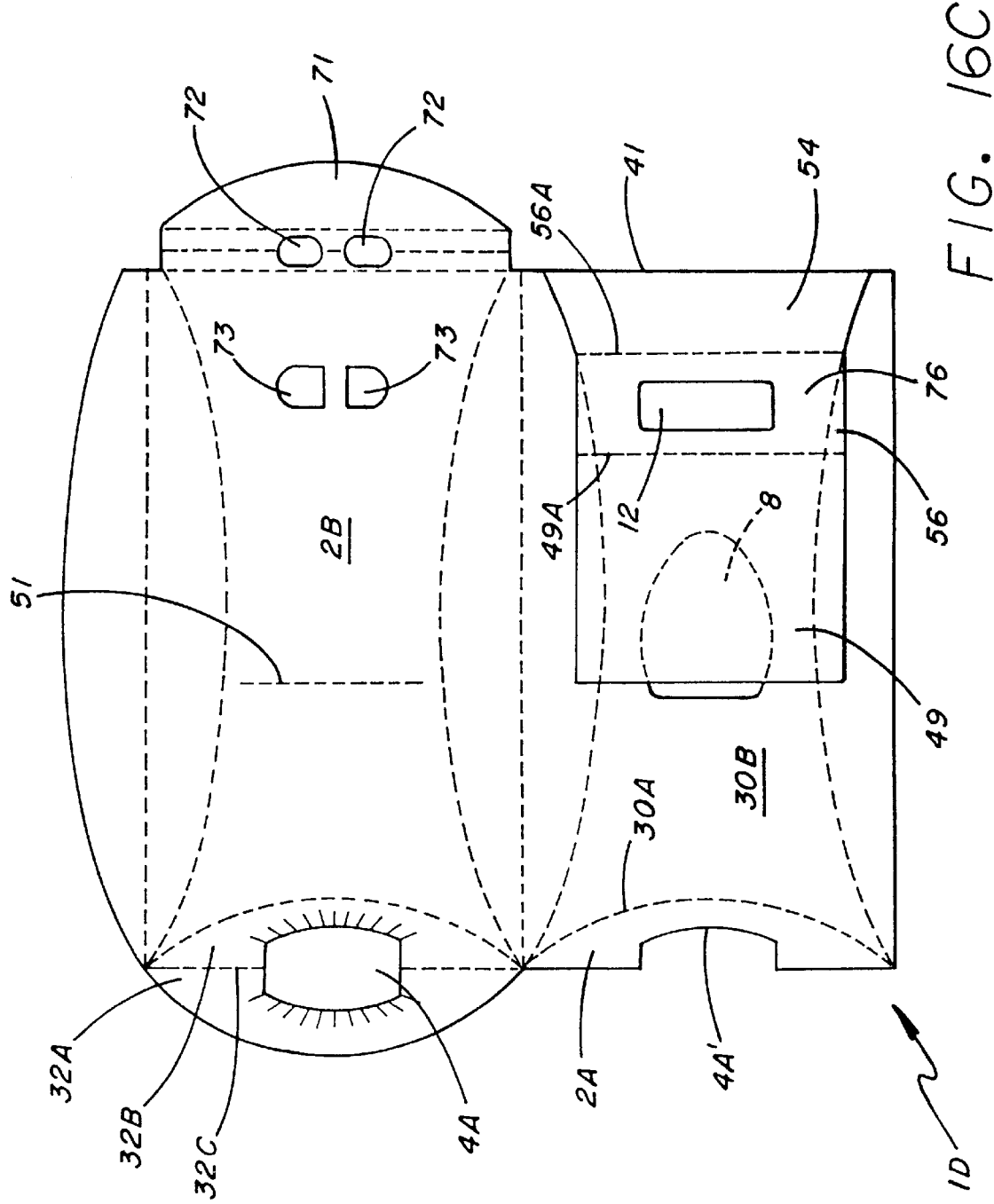
FIG. 16C is a bottom view of the sheet as shown in FIG. 16B and which a portion has been folded back to construct an inhalation valve structure.

FIGS. 16A–C show a single punched-out sheet used to construct a collapsible/expandable valved chamber 1D which, when assembled, "pops up" into the configuration shown in FIGS. 18A and 18B. As in the previously described embodiments, valved chamber 1D includes a bottom section 2, a top section 30, and inner mouthpiece section 53, and an outer mouthpiece section 53B. FIG. 16A shows a plan view of the outer surface of the sheet from which valved chamber 1D is constructed, and FIG. 16B shows a plan view of the inner surface of the sheet.

A main difference between valved chamber 1D and the previously described embodiments is that the various scored fold lines along which the left side section panels and right side section panels are connected to the top section 30B and the bottom section 2B are arcuate fold lines, rather than straight fold lines. Specifically, the left side section includes two left side panels 180A and 180B connected by a straight scored fold line 180C as shown. Left side panel 180A is connected along an arcuate scored fold line 180E to bottom panel 2B, and left side panel 180B is connected along an arcuate scored fold line 180D to top panel 30B. Adhesive attachment panel 47 is connected by an arcuate scored fold line 47E to top panel 30B.

As in the previous embodiments, top panel 30B has a window opening 8 therein, with a piece of transparent membrane adhesively attached to the inner surface of top panel 30B source to provide a sealed, transparent window into the interior of valved chamber 1A. The rear end portion of bottom panel 2B is connected along an arcuate scored fold line 3A to an outer boot adapter panel 32B, which is connected along a straight scored fold line 32C to an outer boot adapter panel 32A having an outer edge which is symmetrical to arcuate fold line 3A. An elongated opening 4A bounded by scalloped sections 4B formed by slits 4C is aligned with half-opening 4B in inner boot adapter panel 2A, which is connected along arcuate scored fold line 30A to the rear end of top panel 30B.

Outer mouthpiece section 53B includes a tab 71 connected along straight scored fold line 71A to an elongated rectangular mouthpiece panel 15B, which is connected along a straight scored fold line 15C to another elongated rectangular mouthpiece panel 15A, which in turn is connected along straight scored fold line 13 to bottom panel 2B.

As in the previous embodiments, mouthpiece holes 72 are centrally formed in mouthpiece panel 15A,B. A pair of exhale valve holes 73 are formed in bottom panel 2B, with an exhale membrane 75 attached along one side of exhale valve holes 73 so as to cover them, and to flex away from them when the user exhales into valved chamber 1D source to allow exhale breath to be exhausted to exhaust valve holes 73 and to seal exhale valve holes 73 when the user inhales through mouthpiece holes 72.

Inner mouthpiece section 53 includes a trapezoidal panel 54 connected along straight scored fold line 41 to top panel 30B. A panel 56 is connected along straight scored fold line 56A to trapezoidal panel 54. An elongated inhale valve hole 12 is centrally formed in panel 56 as shown. An inhale valve membrane 76 is adhesively attached to the surface of trapezoidal panel 54 in FIG. 16A so as to cover inhale valve hole 12 as shown. Adhesive attachment panel 49 is connected along straight scored fold line 49A. A pair of arcuate scored fold lines 49C and 49E connect side section's 49B and 49D to adhesive attachment panel 49 as shown. Fold lines 49C and 49E and the associated sections 49B and 49D provide for convenience of manufacture and reduction of internal air leakage around the inhale valve.

To construct valved chamber 1D, inner mouthpiece section 53 is folded along fold line 41 back against the inner surface of the sheet as shown in FIG. 16C. Inner mouthpiece section 53 also is folded along fold lines 56A and 49A to weaken the fold lines somewhat. Bottom panel 2B is folded along scored fold line 180C underneath top panel 30B so as to be parallel thereto. The outer surface of a portion of the adhesive attachment panel 49 is affixed by suitable adhesive to the inner surface of bottom panel 2B so that the outer edge of adhesive panel 49 is aligned with imaginary dashed line 51, so that panel 56 and mouthpiece valve opening 12 therein can flex relative to top panel 30B and bottom panel 2B to a substantially inclined position relative to a longitudinal axis between mouthpiece holes 72 in the mouthpiece of a boot adapter inserted into opening 4A of outer boot adapter panel. The inner surface of right side panel 47A 32A,B is adhesively attached to the power surface of adhesive attachment panel 47 so that the two panels 47A and 47 are precisely aligned. The inner surface of outer boot adapter panel 32A is adhesively attached to the outer surface of inner boot adapter panel 2A so that the two panels 32A and 2A are precisely aligned, and opening 4A' is precisely aligned with a corresponding half of opening 4A. The inner surface of tab 71 of outer mouthpiece section 53B is adhesively attached to the portion of top panel 30B adjacent to fold line 41 so that fold line 41 is aligned with fold line 71A.

When valved chamber 1D is assembled as described above, it is in its flat or collapsed configuration. If the user presses left side panels 180A and 180B toward right side panels 47A and 47B so that they "on fold" along straight, scored fold lines 180C and 47C, respectively, the valved chamber pops up into the configuration shown in FIGS. 18A and 18B, which show the top and side plan views, respectively, of the valved chamber 1D.

Figure 17B:
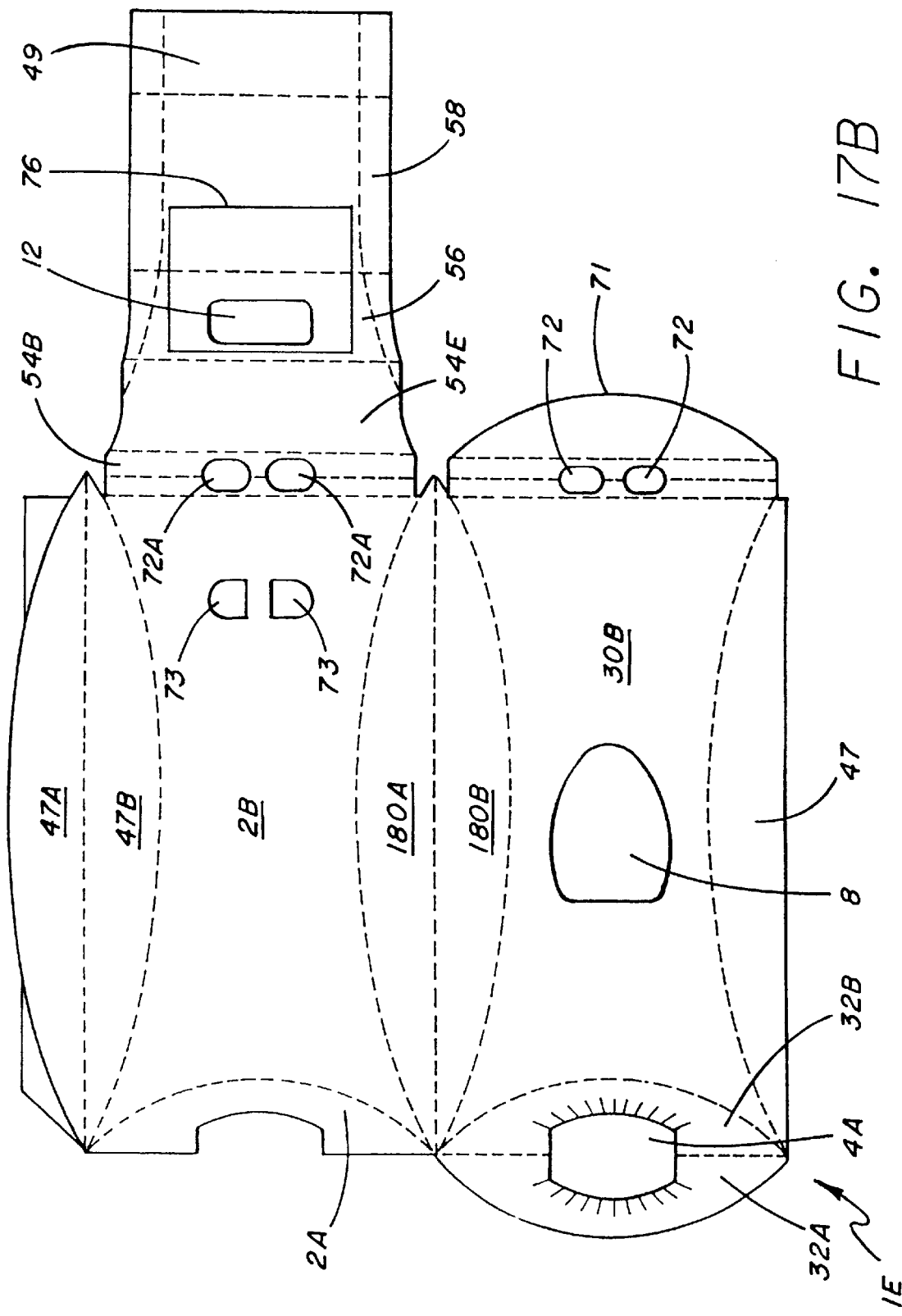
FIG. 17B is a bottom view of the sheet shown in FIG. 17A.
Figure 17C:
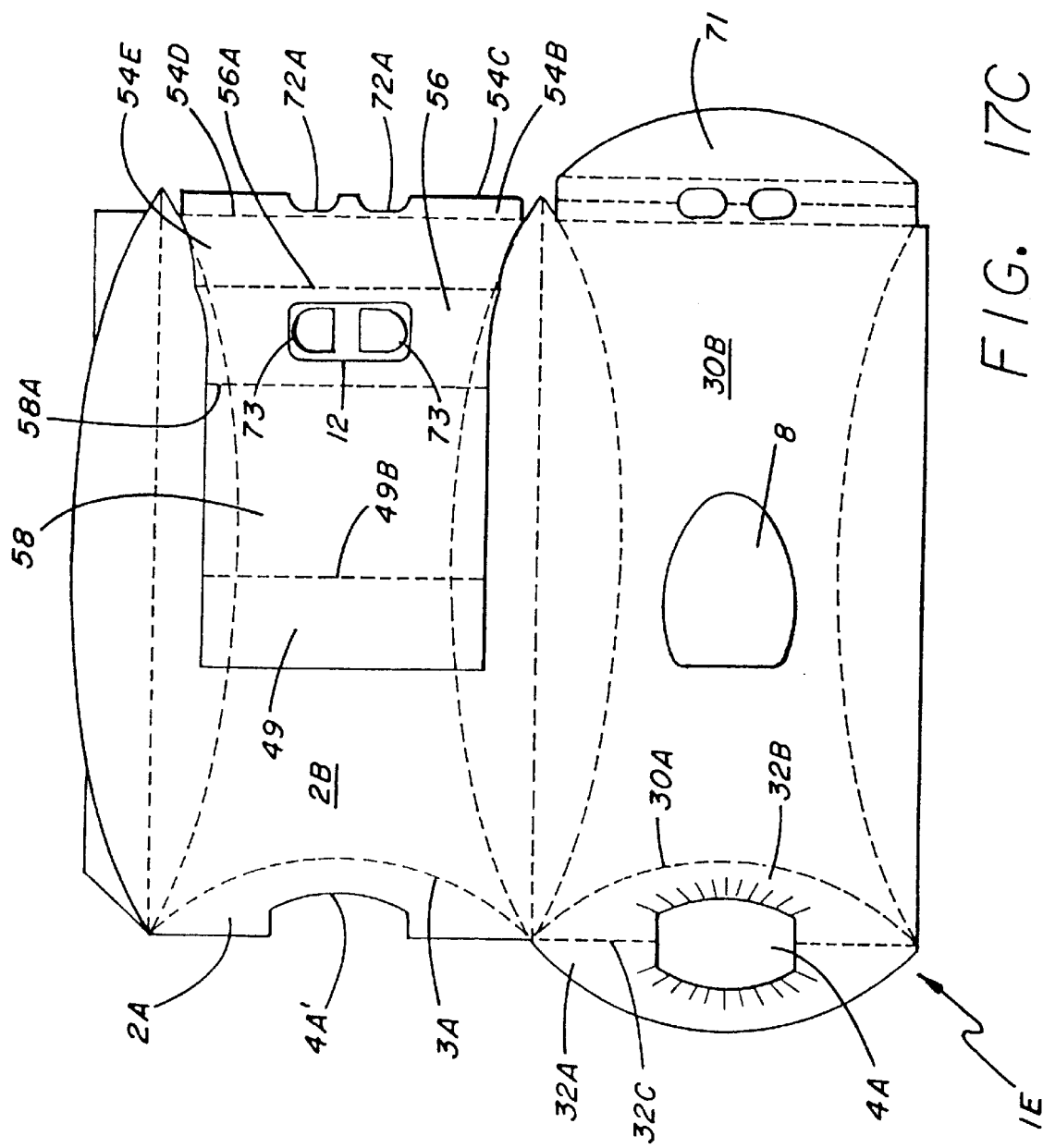
FIG. 17C is a bottom view of the sheet as shown in FIG. 17B and which a portion has been folded back to construct an inhalation valve structure.

FIGS. 17A–C show a single punched-out sheet used to construct a slightly different collapsible/expandable valved chamber 1E which, when assembled, "pops up" in the same manner as valved chamber 1Dg FIGS. 16A–C into the same above-described configuration shown in FIGS. 18A and 18B. Valved chamber 1E includes a bottom section 2, a top section 30, an inner mouthpiece section 53, and an outer mouthpiece section 53B. FIG. 17A shows a plan view of the outer surface of the sheet from which valved chamber 1E is constructed, and FIG. 17B shows a plan view of the inner surface of the sheet. The left side section includes two left side panels 180A and 180B connected by a straight scored fold line 180C as shown. Left side panel 180A is connected along an arcuate scored fold line 180E to bottom panel 2B, and left side panel 180B is connected along an arcuate scored fold line 180D to top panel 30B. Adhesive attachment panel 47 is connected by an arcuate scored fold line 47E to top panel 30B. Top panel 30B has a window opening 8 therein, with a piece of transparent membrane adhesively attached to the inner surface of top panel 30B source to provide a sealed, transparent window into the interior of valved chamber 1A. The rear end portion of bottom panel 2B is connected along an arcuate scored fold line 3A to an inner boot adapter panel 2A. An outer boot adapter panel 32A,B includes a panel 32A which is connected along a straight scored fold line 32C to an outer boot adapter panel 32B which is connected along arcuate scored fold line 30A to the rear end of top panel 30B. A portion of an elongated opening 4A bounded by scalloped sections 4B formed by slits 4C is aligned with a corresponding portion of half-opening 4B in inner boot adapter panel 2A.

Outer mouthpiece section 53B includes a tab 71 connected along straight scored fold line 71A to an elongated rectangular mouthpiece panel 15B, which is connected along a straight scored fold line 15C to another elongated rectangular mouthpiece panel 15A, which in turn is connected along straight scored fold line 13 to top panel 30B. Mouthpiece holes 72 are centrally formed in mouthpiece panel 15A,B.

A pair of exhale valve holes 73 are formed in bottom panel 2B, with an exhale membrane 75 attached as shown in FIG. 17A along one side of exhale valve openings 73 so as to cover them, and to flex away from exhale valve openings 73 when the user exhales into valved chamber 1D, to thereby allow exhaled breath to be exhausted through exhaust valve openings 73, and to seal them closed when the user inhales through mouthpiece holes 72.

Inner mouthpiece section 53 includes an elongated, rectangular panel 54A connected along straight scored fold line 41 to bottom panel 2B and another elongated rectangular panel 54B connected along straight scored fold line 54C to panel 54A. A pair of holes 72A are centrally formed in the panel composed of panels 54A and 54B. A trapezoidal panel 54E is connected along straight scored fold line 54D to two elongated, rectangular panel 54B. A panel 56 is connected along straight scored fold line 56A to trapezoidal panel 54E. An elongated inhale valve hole 12 is centrally formed in panel 56 as shown. An inhale valve membrane 76 is adhesively attached to the inner surface of trapezoidal panel 54 as shown in FIG. 17A so as to cover inhale valve hole 12.

The rectangular panel 58 is connected along straight, scored fold line 58A to trapezoidal panel 56. Adhesive attachment panel 49 is connected along straight scored fold line 49B to rectangular panel 58. A pair of arcuate scored fold lines 49C and 49E connect side sections 49D and 49F to adhesive attachment panel 49 as shown in FIG. 17A.

To construct valved chamber 1E, inner mouthpiece section 53 is folded along fold line 41, and also straight scored fold lines 54C and 54D back against the inner surface of the sheet as shown in FIG. 17C. Inner mouthpiece section 53 also is folded along fold lines 56A, 58A and 49B to weaken those fold lines somewhat. Bottom panel 2B is folded along scored fold line 180C underneath top panel 30B so as to be parallel thereto. The inner surface of a portion of the adhesive attachment panel 49 is affixed by suitable adhesive to the inner surface of bottom panel 2B as shown in FIG. 17C. This connection is made so that panel 56 and mouthpiece valve opening 12 can flex relative to top panel 30B and bottom panel 2B to a substantially inclined position relative to a longitudinal axis between mouthpiece holes 72 and the mouthpiece of a boot adapter inserted into opening 4A of outer boot adapter panel.

The inner surface of right side panel 47A is adhesively attached to the lower surface of adhesive attachment panel 47 so that the two panels 47A and 47 are precisely aligned. The inner surface of outer boot adapter panel 32A is adhesively attached to the outer surface of inner boot adapter panel 2A so that the two panels 32A and 2A are precisely aligned, and opening 4A' is precisely aligned with one-half of opening 4A. The inner surface of tab 71 of outer mouthpiece section 53B is adhesively attached to a portion of top panel 30B adjacent to fold line 41 so that fold line 41 is aligned with fold line 71A.

When valved chamber 1E is assembled as described above, it is in its flat or collapsed configuration. If the user presses left side panels 180A and 180B toward right side panels 47A and 47B so that they "unfold" along straight, scored fold lines 180C and 47C, respectively, the valved chamber pops up into the configuration shown in FIGS. of 18A and 18B, which show the top and side plan views, respectively, of the valved chamber 1E. The fold lines 41, 54C, 54D, 56D and 58A allow the upper edge of panel 56 to be pulled up from a generally horizontal position of panel 56 when valved chamber 1E is collapsed so that panel 56 is in a substantially inclined position when valved chamber 1E is "popped up".

In valved chamber 1E, and also in valved chamber 1D, as the side panels 180A and 180B are pressed inwardly toward the opposite side panels 47A and 47B, those side panels "buckle" inward and remain buckled inward so as to retain valved chamber 1E in its "popped up" configuration.

Figure 19A:
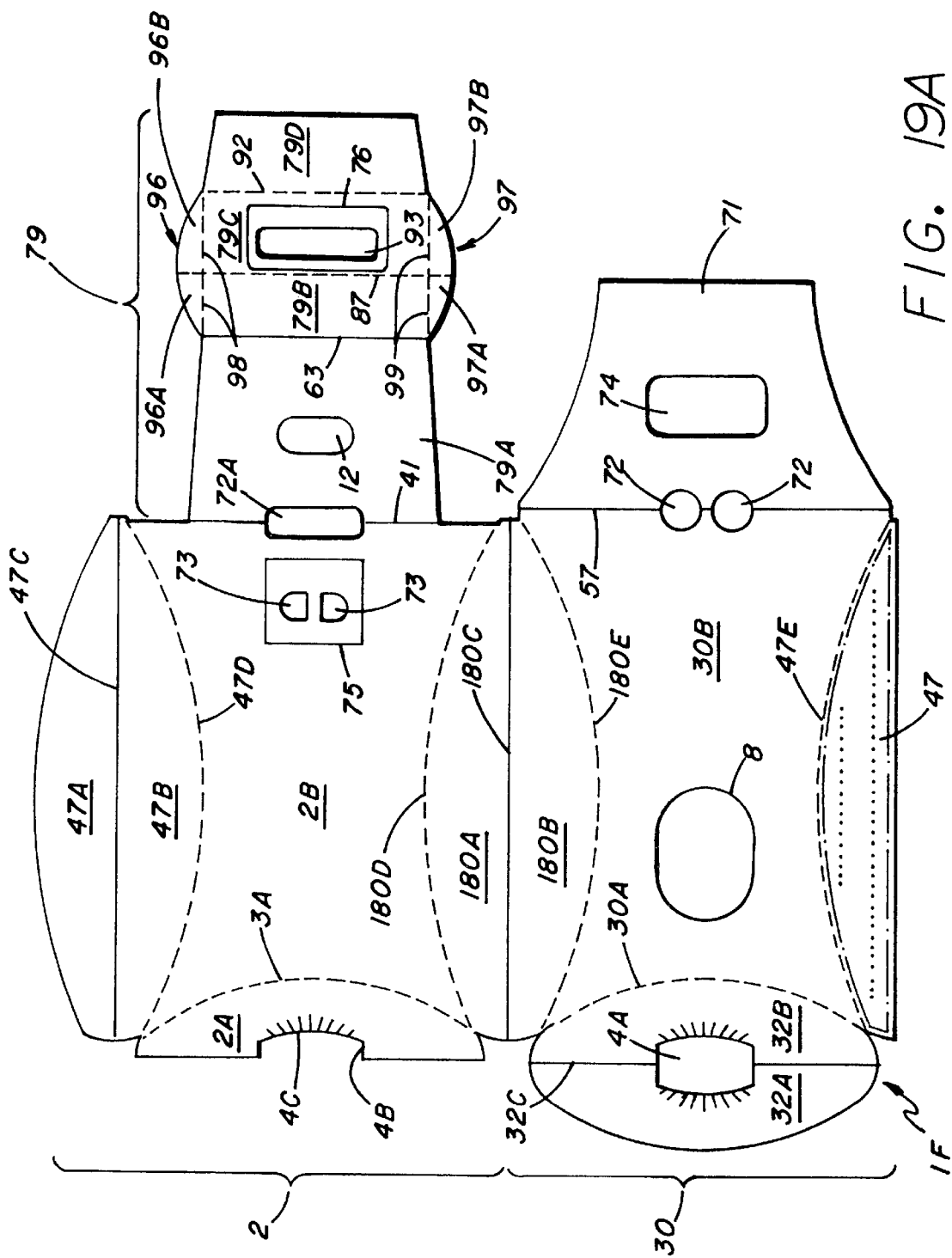
FIG. 19A is a top view, drawn to scale, of the outside surface of a sheet from which a sixth embodiment of the invention is constructed.
Figure 19B:
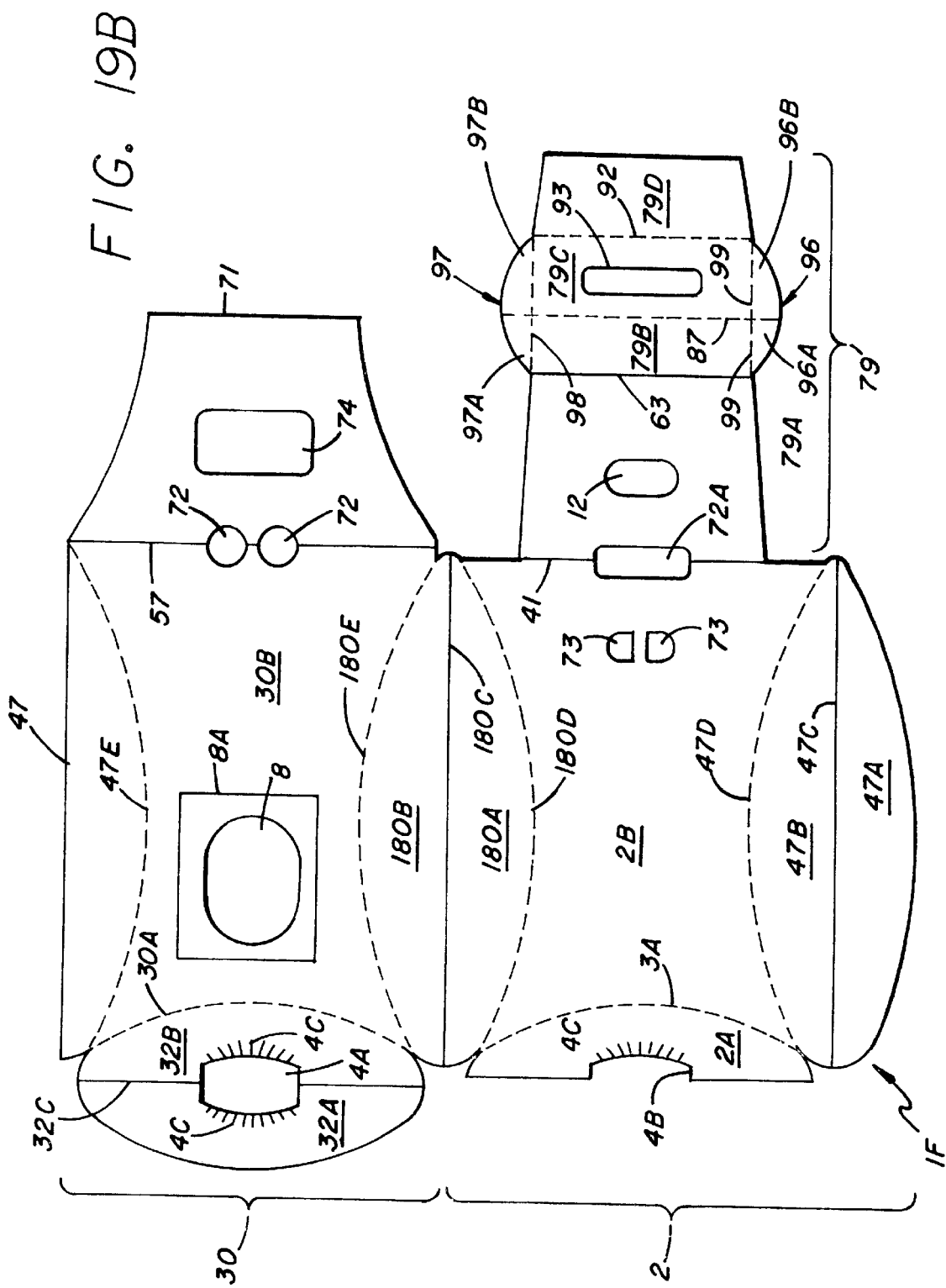
FIG. 19B is a bottom view, drawn to scale, of the sheet shown in FIG. 19A.

FIGS. 19A–C show a single punched-out sheet used to construct another collapsible/expandable valved chamber 1F which, when assembled, "pops up" in a similar but significantly different manner than the valved chamber 1D of FIGS. 16A–C and the valved chamber 1E of FIGS. 17A–C. Valved chamber 1F includes a bottom section 2, a top section 30, an inner mouthpiece section 79, and an outer mouthpiece section 71. FIG. 19A shows a plan view of the outer surface of the sheet 1F from which valved chamber 1F is constructed, and FIG. 19B shows a plan view of the inner surface of sheet 1F. The right side section includes two right side panels 180A and 180B connected by a straight scored fold line 180C as shown. Right side panel 180A is connected along an arcuate "skip-scored" fold line 180D to bottom panel 2B, and right side panel 180B is connected along an arcuate skip-scored fold line 180E to top panel 30B. (A skip-scored fold line includes a sequence of scored and non-scored sections of a fold line having the appearance of dashed line.).

Adhesive attachment panel 47 is connected by an arcuate scored fold line 47E to top panel 30B, and eventually is adhesively attached to the inner surface of left side panel 47A. The "dots" appearing on adhesive attachment panel 47 in FIG. 19A represent small partial perforations which enhance the adhesive attachment.

Top panel 30B has a window opening 8 therein, with a piece of transparent membrane 8A adhesively attached to the inner surface of top panel 30B source to provide a sealed, transparent window into the interior of valved chamber 1A. The rear end portion of bottom panel 2B is connected along an arcuate skip-scored fold line 3A to an inner boot adapter panel 2A. An outer boot adapter panel 32A,B includes a panel 32A which is connected along a straight scored fold line 32C to an outer boot adapter panel 32B which is connected along arcuate skip-scored fold line 30A to the rear end of top panel 30B. A portion of an elongated opening 4A bounded by scalloped sections 4B formed by slits 4C is aligned with a corresponding portion of half-opening 4B in inner boot adapter panel 2A.

Outer mouthpiece section 71 is connected along straight scored fold line 57 to top panel 30B. Circular mouthpiece holes 72 are symmetrically formed in both top panel 30B and outer mouthpiece section 71, so as to be bisected by scored fold line 57.

A pair of exhale valve holes 73 are formed in bottom panel 2B, with an exhale membrane 75 attached as shown in FIG. 19A along one side of exhale valve openings 73 so as to cover them, and to flex away from exhale valve openings 73 when the user exhales into valved chamber 1D, to thereby allow exhaled breath to be exhausted through exhaust valve openings 73, and to seal them closed when the user inhales through mouthpiece holes 72.

Inner mouthpiece section 79 includes an elongated, trapezoidal panel 79A connected along straight scored fold line 41 to bottom panel 2B and a "somewhat trapezoidal" panel 79B connected along a straight scored fold line 63 to panel 79A. An elongated opening 12 in panel 79A becomes aligned with exhale valve openings 73 when panel 79A is folded against the inner surface of bottom panel 2B as shown in subsequently described FIG. 19C.

An elongated rectangular mouthpiece opening 72A is symmetrically formed in bottom panel 2B and inner mouthpiece section panel 79A so as to be bisected by fold line 41. Panel 79B is connected to another somewhat trapezoidal panel 79C along a straight scored fold line 87. A rectangular inhale valve opening 93 is formed centrally in panel 79C. A rectangular inhale valve membrane 76 is adhesively attached to the outer surface of the sheet 1F as shown in FIG. 19A so as to cover inhale valve opening 93 and flex to uncover inhale valve opening 93 is the user inhales through mouthpiece openings 72 and 72A. Panel 79C is attached to trapezoidal panel 79D along a straight skip-scored fold line 92. Preferably, inhale valve opening 93 is as large as can be practically fit into panel 79C while nevertheless providing adequate room both for attachment of inhale membrane 76 to panel 79C and for proper operation of inhale membrane 76.

A "ear" panel 96A,B is connected to panel 79B,C along a straight skip-scored fold line 98A, and another "sealing" panel 97A,B is connected to panel 79B,C along a straight skip-scored fold line 99A. The outer portions of fold line 87 extending through sealing panels 96A,B and 97A,B are continuously scored, rather than skip-scored. The outer edges of sealing panels 96A,B and 97A,B are arcuate, rather than straight, which is why the above mentioned panels 79B and 79C are referred to as "somewhat trapezoidal".

FIGS. 19A–C are drawn to scale. The length of embodiment sheet 1F being developed is 10 and ⅞ inches, and the way is 8 and ²⁷⁄₃₂ inches. The sheet 1F can be composed of SBS paperboard, i.e., solid bleached sulfate paperboard. However, various other materials can be used.

It will be helpful to also refer to FIGS. 19D and 19E to explain how to construct the expandable/collapsible valved chamber 1F as shown in FIGS. 19D and 19E from the single sheet shown in FIGS. 19A–D. First, inner mouthpiece section 79 is folded along fold line 41 back against the inner surface of the sheet 1F as shown in FIG. 19C. The inner surface of trapezoidal panel 79D is folded upward from the configuration shown in FIG. 19C and is adhesively attached to the inner surface of top panel 30B as shown in the section views of FIGS. 19D and 19E.

Bottom panel 2B then is folded along straight scored fold line 180C so as to be underneath and generally parallel to top panel 30B. The outer surface of a portion of the adhesive attachment panel 47 is aligned with and affixed by suitable adhesive to the inner surface of left side panel 47A.

The inner surface of outer boot adapter panel 32A is aligned with and adhesively attached to the outer surface of inner boot adapter panel 2A. The inner surface of outer mouthpiece section 71 is aligned with and adhesively attached to a portion of the outer surface of top panel 30B adjacent to fold line 41 so that fold line 41 is aligned with fold line 57 and opening 12 is aligned with exhale valve openings 73.

When valved chamber 1F is assembled as described above, it is in its flat or collapsed configuration. If the user presses right side panels 180A and 180B inward toward left side panels 47A and 47B so that they "unfold" along straight, scored fold lines 180C and 47C, respectively, the valved chamber pops up into and retains the configuration shown in FIG. 19E. The fold lines 41, 63, 87, and 92 allow panels 79B and 79C to be pulled by adhesive and 79D and the rising upper panel 30B upward from their generally horizontal position when valved chamber 1F is collapsed so that the panel 79B,C is in a nearly vertical position when valved chamber 1F is fully "popped up".

As this unfolding occurs, and as right side panels 180A and 180B move inward and engage sealing panels 97A and 97B, sealing panels 97A and 97B also are pressed inward. This causes sealing panels 97A and 97B to fold forward along fold line 98 into the configuration shown in FIG. 19E. Similarly, as left side panels 47A and 47B move inward and engage sealing panels 96A and 96B, sealing panels 96A and 96B also are pressed inward. This causes sealing panels 96A and 96B to fold forward along fold line 99 into a configuration which is the mirror image of that shown in FIG. 19E. Thus, sealing panels 96A,B form a good seal with left side panels 47A and 47B, and sealing panels 97A,B form a good seal with right side panels 180A and 180B and thereby effectively prevent both inhaled air and exhaled air from bypassing the inhalation valve. This substantially increases the efficiency of the valved chamber 1F, by preventing air inadvertently exhaled (rather than inhaled) by a patient during activation of an MDI canister in a boot adapter (not shown) inserted into opening 4A of boot adapter panel 32A,B from being forced around panels 79B and 79C of inhalation valve assembly 79 into the large volume between it and boot adapter panel 32A,B. This prevents the inadvertently exhaled air from forcing some of the MDI medication to leak out into the atmosphere between the periphery of opening 4A and the periphery of the MDI boot adapter. The efficiency of the valved chamber 1F is thereby increased substantially.

Figure 19F:
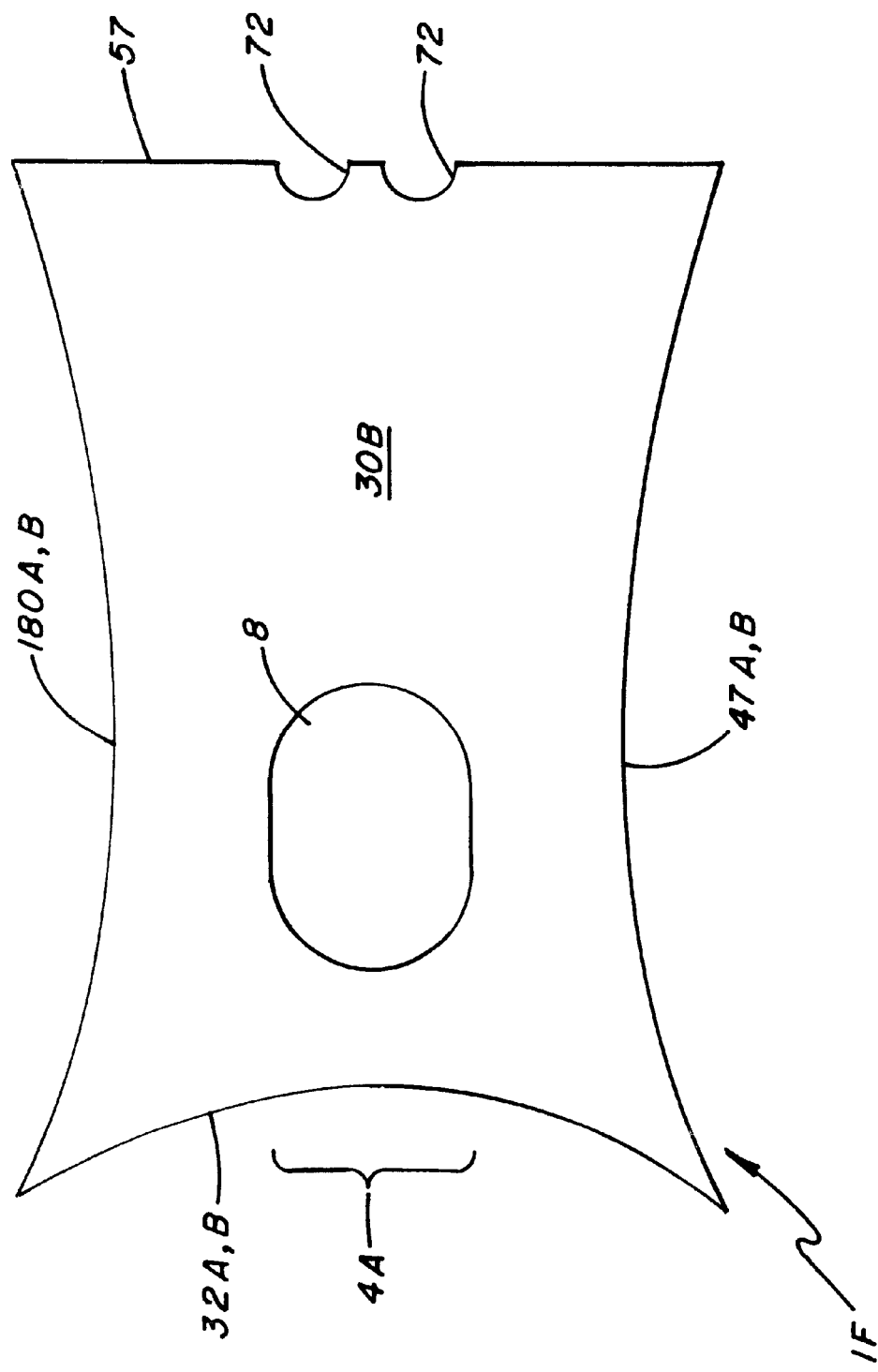
FIG. 19F is a top plan view of the collapsible/expandable valved chamber of FIGS. 19A–19E in its fully "popped up" configuration.

When the boot adapter 77 (with an MDI canister 78 therein), shown in dashed lines in FIG. 19E, is inserted into opening 4A, that causes boot adapter panels 32A and 32B to unfold to the maximum extent, producing the centerline sectional view of FIG. 19E. FIG. 19F shows the resulting top plan view of the collapsible/expandable valved chamber 1F resulting from both popping the valved chamber of and inserting boot adapter 77.

The structure shown in FIGS. 19A–F has a larger ratio of the volume of the region shown to the left of panel 79B,C in FIG. 19E to the volume of the region shown to the right of panel 79B,C than is the case for the other disclosed embodiments. This results in improved efficiency, that is, higher percentage of the MDI medication reaching the target medication sites in the patient lungs.

The invention thus provides an improved valved chamber in which the inhalation flap opens the inhale air path as the patient inhales. The exhalation valve hole 73 and exhalation valve membrane 75 present very low resistance to exhaled air flow, so the patient is not so likely to feel a need to remove the chamber from his/her mouth during the exhalation that precedes actuation and inhalation. Therefore, with suitable instruction, most patients can easily synchronize inhalation with actuation of the MDI canister, because of the smaller number of steps that the patient must coordinate during the critical few seconds while the medication is being delivered.

Thus, the invention provides a disposable "pop up" valved chamber which also allows for natural inhalation and exhalation by the patient. The described valved chamber device can be maintained in a collapsed, flat configuration, suitable for storage in a suit coat pocket or a briefcase, and expanded immediately prior to use, after which it can be discarded or re-folded for later use by the same patient. The described valved chamber is ideal for use as a training aid to allow a health care worker to demonstrate its use to patients needing to receive an aerosol medication from an MDI inhaler. The invention also is well suited for use in hospital emergency rooms, health-care clinics, pulmonary function labs, or infirmaries. In addition, its portability and low cost make it ideal for use by relief or world health organizations, especially when aerosol vaccines become available.

While the invention has been described with reference to several particular embodiments thereof, those skilled in the art will be able to make the various modifications to the described embodiments of the invention without departing from the true spirit and scope of the invention. It is intended that all elements or steps which are insubstantially different or perform substantially the same function in substantially the same way to achieve the same result as what is claimed are within the scope of the invention. For example, an exhalation port could be provided in the wall of the mouthpiece section instead of using the disclosed one-way exhalation valve 73,75. Various other ways of folding the sheet material to achieve the collapsed/expanded configurations can be provided. Different arrangements of lock tabs and lock tab receiving slots than disclosed herein could be provided, or velcro or similar attachment materials could be used.

What is claimed is:

1. A medication inhalation apparatus, comprising:
   (a) a collapsible/expandable housing that is collapsible into a substantially flat configuration and expandable to bound a first volume and a second volume, the first volume receiving a plume of medication particles ejected by an MDI inhaler;
   (b) an inhalation/exhalation opening in an inhalation/exhalation end of the housing for allowing inhalation from the second volume by a patient and allowing exhalation into the second volume by the patient;
   (c) a collapsible boot adapter panel connected to an inlet end of the housing, and an opening for receiving a mouthpiece of the MDI inhaler;
   (d) a collapsible one-way inhalation valve assembly disposed between the first volume in the second volume for allowing one-way flow of gas from the first volume through the second volume to the inhalation/exhalation opening;

the housing including a first foldable side section including a first fold line and a second foldable side section including a second fold line, the first foldable side section including a first side panel connected along a third fold line to a top panel and a second side panel connected along a fourth fold line to a bottom panel, the second foldable side section including a third side panel connected along a fifth fold line to the bottom panel and a fourth side panel connected along a sixth fold line to the top panel, wherein simultaneously pressing the first and second foldable side sections inward on fold the first and second foldable sections along the first and second fold line, respectively, to expand the housing, the inhalation valve assembly including an inhalation flap and a valve seat, whereby exhalation by the patient through the inhalation/exhalation opening presses the inhalation flap against the valve seat to prevent flow of exhaled gas into the first volume, inhalation by the patient through the inhalation/exhalation opening causing a portion of the inhalation flap to move away from the valve seat to provide a path for flow of gas from the first volume into a second volume between the inhalation valve assembly and inhalation/exhalation opening.

2. A medication inhalation apparatus, comprising:
   (a) a collapsible/expandable housing that is collapsible into a substantially flat configuration and expandable to bound a first volume and a second volume, the first volume receiving a plume of medication particles ejected by an MDI inhaler;
   (b) an inhalation/exhalation opening in an inhalation/exhalation end of the housing for allowing inhalation from the second volume by a patient and allowing exhalation into the second volume by the patient;
   (c) a collapsible boot adapter panel connected to an inlet end of the housing, and an opening for receiving a mouthpiece of the MDI inhaler;
   (d) a collapsible one-way inhalation valve assembly disposed between the first volume in the second volume for allowing one-way flow of gas from the first volume through the second volume to the inhalation/exhalation opening;
   (e) an exhalation valve assembly disposed in a wall of the housing for allowing one-way flow of gas exhaled to the inhalation/exhalation opening from the second volume to the outside atmosphere;

the housing including a first foldable side section including a first fold line and a second foldable side section including a second fold line, the first foldable side section including a first side panel connected along a third fold line to a top panel and a second side panel connected along a fourth fold line to a bottom panel, the second foldable side section including a third side panel connected along a fifth fold line to the bottom panel and a fourth side panel connected along a sixth fold line to the top panel, wherein simultaneously pressing the first and second foldable side sections inward on fold the first and second foldable sections along the first and second fold line, respectively, to expand the housing, the inhalation valve assembly including an inhalation flap and a valve seat, whereby exhalation by the patient through the inhalation/exhalation opening presses the inhalation flap against the valve seat to prevent flow of exhaled gas into the first volume, inhalation by the patient through the inhalation/exhalation opening causing a portion of the inhalation flap to move away from the valve seat to provide a path for flow of gas from the first volume into a second volume between the inhalation valve assembly and inhalation/exhalation opening.

3. The medication inhalation apparatus of claim 2 wherein the first and second fold lines are substantially straight when the housing is in a collapsed configuration.

4. The medical inhalation apparatus of claim 3 wherein the third, fourth, fifth, and sixth fold lines are arcuate.

5. The medical inhalation apparatus of claim 3 wherein curvature of the third, fourth, fifth and sixth fold lines causes bending of the first, second, third, and fourth side panels as they are pressed together to expand the housing such that the first, second, third, and fourth side panels remain bent and retain the housing in the expanded configuration when pressure is no longer being applied to press the first and second foldable side sections inward.

6. The medication inhalation apparatus of claim 2 wherein the inhalation valve assembly forms a wall separating the first volume from the second volume when the housing and the inhalation valve assembly are in the expanded configuration.

7. The medical inhalation apparatus of claim 2 wherein the inhalation valve assembly includes a first panel connected by a seventh fold line to an outlet end edge of the bottom panel, a first generally trapezoidal panel connected by an eighth fold line to the first panel, a second generally trapezoidal panel connected by a ninth fold line to the first generally trapezoidal panel, and an adhesive tab connected by a tenth fold line to the second generally trapezoidal panel the first and second generally trapezoidal panels each including foldable sealing panels which are engaged by the first and second foldable side sections to form seals to prevent inhaled gas from bypassing the inhalation valve assembly.

8. The medical inhalation apparatus of claim 2 wherein the inhalation valve assembly includes first and second foldable sealing panels which are engaged by the first and second foldable side sections, respectively, such that the first and second sealing panels fold against and form seals with the first and second foldable side sections, respectively, to prevent inhaled gas and exhaled gas from bypassing the inhalation valve assembly.

9. The medication inhalation apparatus of claim 2 wherein the housing and the inhalation of assembly are integral and are composed of a single piece of material from the group consisting of paper and plastic.

10. The medical inhalation apparatus of claim 9 wherein the single piece of material is composed of solid bleached sulfate paperboard.

11. The medical inhalation apparatus of claim 9 wherein the first and second fold lines are continuously scored.

12. The medical inhalation apparatus of claim 9 wherein the third, fourth, fifth, and sixth fold lines are skip-scored.

13. The medication inhalation apparatus of claim 9 wherein the inhalation valve assembly is attached along a fold line to an edge of the bottom panel.

14. The medication inhalation apparatus of claim 2 wherein the boot adapter panel includes an inner boot adapter panel attached to an inlet end of one of the top panel and the bottom panel and having a cutout therein and an outer boot adapter panel attached to an inlet end of the other of the top panel and the bottom panel, the cutout of the inner boot adapter panel being aligned with the opening of the outer boot adapter panel when the housing is expanded, the outer boot adapter panel being adhesively attached to the inner boot adapter panel.

15. The medication inhalation apparatus of claim 14 wherein the opening of the boot adapter panel has a slitted peripheral portion for adapting to receive different sized mouthpieces of various MDI inhalers.

16. The medication inhalation apparatus of claim 14 wherein the inhalation valve assembly is attached along a fold line to an edge of one of the bottom panel and a top panel, and an outer tab is attached along a fold line to an edge of the other of the top panel and the bottom panel.

17. The medication inhalation apparatus of claim 5 wherein the exhalation valve assembly is disposed in the bottom panel.

18. The medication inhalation apparatus of claim 2 wherein the top panel includes a viewing hole and a sheet of transparent material attached to form a seal around the periphery of the viewing hole to provide a viewing window into the first volume.

19. A method of expanding a medication inhalation apparatus from an initially flat, collapsed configuration, comprising:
(a) providing
  i. a housing in the collapsed configuration, an inhalation/exhalation opening being disposed at an outlet end of the housing,
  ii. a collapsible/expandable one-way inhalation valve assembly in the housing for allowing one-way flow of gas from within the housing when it is expanded through the inhalation/exhalation opening during inhalation by a patient, and
  iii. a collapsible/expandable boot adapter panel connected to an inlet end of the housing, and an opening in the boot adapter panel for receiving a mouthpiece of an MDI inhaler, the inhalation valve assembly including an inhalation flap and a valve seat, an exhalation by the patient through the inhalation/exhalation opening when the housing is expanded pressing the inhalation flap against the valve seat to prevent flow of exhaled gas through the inhalation valve assembly, the exhaled gas flowing through an opening in the housing between the inhalation valve assembly and the inhalation/exhalation opening; and
(b) manually expanding the housing, the inhalation valve assembly, and the boot adapter panel by pressing a pair of foldable side panels on opposite sides of the housing to unfold the side panels causing a top panel of the housing to be pushed away from a bottom panel of the housing and simultaneously forcing a portion of the inhalation valve assembly to unfold to provide a nearly vertical wall that separates a first volume between the inhalation valve assembly and the boot adapter panel and a second volume between the inhalation of assembly and the inhalation/exhalation opening.

20. The method of claim 19 including providing first and second foldable sealing panels attached along corresponding fold lines to the inhalation valve assembly, and engaging the first and second foldable sealing panels with the first and second foldable side sections, respectively, during the manual expanding of step (b) such that the first and second foldable sealing panels fold against and form seals with the first and second foldable side sections, respectively, to prevent inhaled gas from bypassing the inhalation valve assembly.

* * * * *